United States Patent
Li et al.

(10) Patent No.: US 9,324,957 B2
(45) Date of Patent: Apr. 26, 2016

(54) SYNTHESIS OF FOUR COORDINATED GOLD COMPLEXES AND THEIR APPLICATIONS IN LIGHT EMITTING DEVICES THEREOF

(75) Inventors: Jian Li, Phoenix, AZ (US); Eric Turner, Phoenix, AZ (US)

(73) Assignee: Arizona Board of Regents on behalf of Arizona State University, Scottsdale, AZ (US)

( * ) Notice: Subject to any disclaimer, the term of this patent is extended or adjusted under 35 U.S.C. 154(b) by 0 days.

(21) Appl. No.: 13/695,338

(22) PCT Filed: May 2, 2011

(86) PCT No.: PCT/US2011/034782
§ 371 (c)(1),
(2), (4) Date: May 16, 2013

(87) PCT Pub. No.: WO2011/137431
PCT Pub. Date: Nov. 3, 2011

(65) Prior Publication Data
US 2013/0237706 A1  Sep. 12, 2013

Related U.S. Application Data

(60) Provisional application No. 61/329,687, filed on Apr. 30, 2010.

(51) Int. Cl.
| | | |
|---|---|---|
| *H01L 51/00* | (2006.01) | |
| *C07D 213/643* | (2006.01) | |
| *C07F 1/00* | (2006.01) | |
| *C09K 11/06* | (2006.01) | |
| *H05B 33/14* | (2006.01) | |
| *H01L 51/42* | (2006.01) | |
| *H01L 51/50* | (2006.01) | |

(52) U.S. Cl.
CPC ........ *H01L 51/0084* (2013.01); *C07D 213/643* (2013.01); *C07F 1/00* (2013.01); *C09K 11/06* (2013.01); *H01L 51/0091* (2013.01); *H05B 33/14* (2013.01); *C09K 2211/1029* (2013.01); *C09K 2211/1044* (2013.01); *C09K 2211/1059* (2013.01); *C09K 2211/188* (2013.01); *H01L 51/424* (2013.01); *H01L 51/5016* (2013.01); *Y02E 10/549* (2013.01)

(58) Field of Classification Search
None
See application file for complete search history.

(56) References Cited

U.S. PATENT DOCUMENTS

| | | | |
|---|---|---|---|
| 6,780,528 B2 | 8/2004 | Tsuboyama et al. | |
| 7,002,013 B1 | 2/2006 | Chi et al. | |
| 7,442,797 B2 | 10/2008 | Itoh et al. | |
| 7,501,190 B2 | 3/2009 | Ise | |
| 7,655,322 B2 | 2/2010 | Forrest et al. | |
| 7,947,383 B2 | 5/2011 | Ise et al. | |
| 8,816,080 B2 | 8/2014 | Li et al. | |
| 8,927,713 B2 | 1/2015 | Li et al. | |
| 8,946,417 B2 | 2/2015 | Jian et al. | |
| 9,059,412 B2 | 6/2015 | Zeng et al. | |
| 2002/0068190 A1 | 6/2002 | Tsuboyama et al. | |
| 2005/0260446 A1 | 11/2005 | Mackenzie et al. | |
| 2006/0202197 A1 | 9/2006 | Nakayama et al. | |
| 2006/0210831 A1 | 9/2006 | Sano et al. | |
| 2006/0263635 A1 | 11/2006 | Ise | |
| 2006/0286406 A1 | 12/2006 | Igarashi et al. | |
| 2007/0057630 A1 | 3/2007 | Nishita et al. | |
| 2007/0059551 A1 | 3/2007 | Yamazaki | |
| 2007/0082284 A1* | 4/2007 | Stoessel et al. | 430/84 |
| 2008/0001530 A1 | 1/2008 | Ise et al. | |
| 2008/0036373 A1 | 2/2008 | Itoh et al. | |
| 2008/0054799 A1 | 3/2008 | Satou | |
| 2008/0079358 A1 | 4/2008 | Satou | |
| 2008/0241518 A1 | 10/2008 | Satou et al. | |
| 2008/0241589 A1 | 10/2008 | Fukunaga et al. | |
| 2009/0026936 A1 | 1/2009 | Satou et al. | |
| 2009/0026939 A1 | 1/2009 | Kinoshita et al. | |
| 2009/0032989 A1 | 2/2009 | Karim et al. | |
| 2009/0039768 A1 | 2/2009 | Igarashi et al. | |
| 2009/0128008 A1 | 5/2009 | Ise et al. | |
| 2009/0218561 A1 | 9/2009 | Kitamura et al. | |
| 2009/0261721 A1 | 10/2009 | Murakami et al. | |
| 2009/0267500 A1 | 10/2009 | Kinoshita et al. | |
| 2010/0000606 A1 | 1/2010 | Thompson et al. | |
| 2010/0013386 A1 | 1/2010 | Thompson et al. | |
| 2010/0171511 A1 | 7/2010 | Takada et al. | |
| 2010/0297522 A1 | 11/2010 | Creeth et al. | |
| 2012/0095232 A1* | 4/2012 | Li et al. | 546/4 |
| 2012/0181528 A1 | 7/2012 | Takada et al. | |
| 2012/0215001 A1 | 8/2012 | Li et al. | |

(Continued)

FOREIGN PATENT DOCUMENTS

| | | |
|---|---|---|
| CN | 1777663 A | 5/2006 |
| CN | 1894269 A | 1/2007 |

(Continued)

OTHER PUBLICATIONS

International Preliminary Report on Patentability issued on Nov. 6, 2012 for Intl. Pat. App. No. PCT/US2011/034782 filed May 2, 2011 and published as WO 2011/137431 on Nov. 3, 2011 (Applicants—Arizona Board of Regents for and on Behalf of Arizona State University; Inventors—Turner et al.;) (6 pages).

International Search Report mailed on Feb. 9, 2013 for Intl. Pat. App. No. PCT/US2011/034782 filed May 2, 2011 and published as WO 2011/137431 on Nov. 3, 2011 (Applicants—Arizona Board of Regents for and on Behalf of Arizona State University; Inventors—Turner et al.;) (3 pages).

Written Opinion mailed on Feb. 9, 2012 for Intl. Pat. App. No. PCT/US2011/034782 filed May 2, 2011 and published as WO 2011/137431 on Nov. 3, 2011 (Applicants—Arizona Board of Regents for and on Behalf of Arizona State University; Inventors—Turner et al.;) (5 pages).

(Continued)

*Primary Examiner* — Timothy R Rozof
(74) *Attorney, Agent, or Firm* — Fish & Richardson P.C.

(57) ABSTRACT

Synthesis of four coordinated gold complexes and their applications in light emitting devices thereof.

11 Claims, 4 Drawing Sheets

(56) References Cited

U.S. PATENT DOCUMENTS

| | | |
|---|---|---|
| 2012/0302753 A1 | 11/2012 | Li |
| 2013/0048963 A1 | 2/2013 | Beers et al. |
| 2013/0168656 A1 | 7/2013 | Tsai et al. |
| 2013/0203996 A1 | 8/2013 | Li et al. |
| 2013/0341600 A1 | 12/2013 | Lin et al. |
| 2014/0014922 A1 | 1/2014 | Lin et al. |
| 2014/0027733 A1 | 1/2014 | Zeng et al. |
| 2014/0084261 A1 | 3/2014 | Brooks et al. |
| 2014/0114072 A1 | 4/2014 | Li et al. |
| 2014/0330019 A1 | 11/2014 | Li et al. |
| 2014/0364605 A1 | 12/2014 | Li et al. |
| 2015/0008419 A1 | 1/2015 | Li |
| 2015/0105556 A1 | 4/2015 | Li et al. |
| 2015/0162552 A1 | 6/2015 | Li et al. |
| 2015/0228914 A1 | 8/2015 | Li et al. |
| 2015/0318500 A1 | 11/2015 | Li et al. |

FOREIGN PATENT DOCUMENTS

| | | |
|---|---|---|
| CN | 101142223 A | 3/2008 |
| CN | 101667626 A | 3/2010 |
| CN | 102449108 A | 5/2012 |
| CN | 102892860 A | 1/2013 |
| CN | 102971396 A | 3/2013 |
| CN | 104232076 A | 12/2014 |
| EP | 1808052 | 7/2007 |
| EP | 1874893 | 1/2008 |
| EP | 1874894 | 1/2008 |
| EP | 1919928 | 5/2008 |
| EP | 2096690 A2 | 9/2009 |
| EP | 2036907 B1 | 2/2012 |
| EP | 2417217 | 2/2012 |
| EP | 2112213 | 7/2012 |
| EP | 2711999 A2 | 3/2014 |
| JP | 2005267557 A | 9/2005 |
| JP | 2005310733 A | 11/2005 |
| JP | 2006047240 A | 2/2006 |
| JP | 2006232784 A | 9/2006 |
| JP | 2006242080 A | 9/2006 |
| JP | 2006242081 A | 9/2006 |
| JP | 2006256999 A | 9/2006 |
| JP | 2006257238 A | 9/2006 |
| JP | 2006261623 A | 9/2006 |
| JP | 2006290988 | 10/2006 |
| JP | 2006313796 A | 11/2006 |
| JP | 2006332622 A | 12/2006 |
| JP | 2006351638 A | 12/2006 |
| JP | 2007019462 A | 1/2007 |
| JP | 2007042875 A | 2/2007 |
| JP | 2007053132 A | 3/2007 |
| JP | 2007066581 A | 3/2007 |
| JP | 2007073620 A | 3/2007 |
| JP | 2007073845 A | 3/2007 |
| JP | 2007073900 A | 3/2007 |
| JP | 2007080593 A | 3/2007 |
| JP | 2007080677 A | 3/2007 |
| JP | 2007088105 A | 4/2007 |
| JP | 2007088164 A | 4/2007 |
| JP | 2007096259 A | 4/2007 |
| JP | 2007110067 A | 4/2007 |
| JP | 2007110102 A | 4/2007 |
| JP | 2007258550 A | 10/2007 |
| JP | 2007324309 A | 12/2007 |
| JP | 2008010353 A | 1/2008 |
| JP | 2008091860 A | 4/2008 |
| JP | 2008103535 A | 5/2008 |
| JP | 2008108617 A | 5/2008 |
| JP | 2008109085 A | 5/2008 |
| JP | 2008109103 A | 5/2008 |
| JP | 2008160087 A | 7/2008 |
| JP | 2008198801 A | 8/2008 |
| JP | 2008270729 A | 11/2008 |
| JP | 2008270736 A | 11/2008 |
| JP | 2009016184 A | 1/2009 |
| JP | 2009016579 A | 1/2009 |
| JP | 2009032977 A | 2/2009 |
| JP | 2009032988 A | 2/2009 |
| JP | 2009267171 | 11/2009 |
| JP | 2009267244 | 11/2009 |
| JP | 2009272339 A | 11/2009 |
| JP | 2009283891 | 12/2009 |
| JP | 2010135689 | 6/2010 |
| JP | 2012222255 A | 11/2012 |
| JP | 2013525436 A | 6/2013 |
| JP | 5604505 | 10/2014 |
| JP | 2014221807 | 11/2014 |
| JP | 2015081257 A | 4/2015 |
| KR | 1020060115371 | 11/2006 |
| KR | 2007061830 | 6/2007 |
| KR | 2007112465 | 11/2007 |
| KR | 1020130043460 | 4/2013 |
| TW | 200701835 | 1/2007 |
| TW | 201307365 | 2/2013 |
| WO | WO-00/70655 A2 | 11/2000 |
| WO | WO0070655 | 11/2000 |
| WO | WO-2004/108857 A1 | 12/2004 |
| WO | WO 2004108857 | 12/2004 |
| WO | WO-2005/042444 A2 | 5/2005 |
| WO | WO-2005/042550 A1 | 5/2005 |
| WO | WO2006033440 | 3/2006 |
| WO | WO2006/098505 | 9/2006 |
| WO | WO2006/115299 | 11/2006 |
| WO | WO2006/115301 | 11/2006 |
| WO | WO2007034985 A1 | 3/2007 |
| WO | WO2007069498 | 6/2007 |
| WO | WO2008/066192 | 6/2008 |
| WO | WO2008/066195 | 6/2008 |
| WO | WO2008/066196 | 6/2008 |
| WO | WO2008/117889 | 10/2008 |
| WO | WO2008/123540 A2 | 10/2008 |
| WO | WO2009/017211 | 2/2009 |
| WO | WO2010118026 | 10/2010 |
| WO | WO2011137429 | 11/2011 |
| WO | WO2011137431 A3 | 4/2012 |
| WO | WO2012112853 | 8/2012 |
| WO | WO2012142387 A1 | 10/2012 |
| WO | WO2012162488 | 11/2012 |
| WO | WO2012163471 | 12/2012 |
| WO | WO2013130483 | 9/2013 |
| WO | WO2014031977 | 2/2014 |
| WO | WO2014047616 | 3/2014 |
| WO | WO2014109814 | 7/2014 |
| WO | WO2015027060 A1 | 2/2015 |

OTHER PUBLICATIONS

First Office Action issued on Jun. 26, 2013 by the Chinese patent Office for Application No. 201080024040.X filed Apr. 6, 2010 (Applicant—Arizona Board of Regents/Inventors—Jian Li, et al.) (pp. 1-16).

Official Communication issued by the European Patent Office on Oct. 2, 2012 for Application No. 10762301.9 filed Apr. 6, 2010 (Applicant—Arizona Board of Regents/Inventors—Jian Li, et al.) (p. 1).

Extended Search Report issued by the European Patent Office on Sep. 13, 2012 for Application No. 10762301.9 filed Apr. 6, 2010 (Applicant—Arizona Board of Regents/Inventors—Jian Li, et al.)(pp. 1-7).

Amendments Received Before Examination filed with the European Patent Office on Mar. 9, 2012 for Application No. 10762301 filed Apr. 6, 2010 (Applicant—Arizona Board of Regents/Inventors—Jian Li, et al.)(pp. 1-8).

Official Communication issued by the European Patent Office on Dec. 7, 2011 for Application No. 10762301.9 filed Apr. 6, 2010 (Applicant—Arizona Board of Regents/Inventors—Jian Li, et al.) (pp. 1-2).

International Preliminary Report on Patentability issued by the International Searching Authority on Oct. 11, 2011 for PCT/US2010/030095 filed Apr. 6, 2010 and published as WO 2010/118026 on Oct. 14, 2010 (Applicant—Arizona Board of Regents/Inventors—Jian Li, et al.) (pp. 1-5).

(56) References Cited

OTHER PUBLICATIONS

International Search Report mailed by the International Searching Authority on Nov. 16, 2010 for PCT/US2010/030095 filed Apr. 6, 2010 and published as WO 2010/118026 on Oct. 14, 2010 (Applicant—Arizona Board of Regents/Inventors—Jian Li, et al.) (pp. 1-4).
Written Opinion issued by the International Searching Authority on Nov. 16, 2010 for PCT/US2010/030095 filed Apr. 6, 2010 and published as WO 2010/118026 on Oct. 14, 2010 (Applicant—Arizona Board of Regents/Inventors—Jian Li, et al.) (pp. 1-4).
Second Office Action issued by the Chinese Patent Office on Mar. 7, 2014 for Pat. App. No. 20108002404.X filed Apr. 6, 2010 and published as CN 102449108A on May 9, 2012 (Applicants—Arizona Technology Enterprises (AZTE); Inventors—Li et al.; (6 pages).
English Translation of Second Office Action issued by the Chinese Patent Office on Mar. 7, 2014 for Pat. App. No. 201080024040.X filed Apr. 6, 2010 and published as CN 102449108A on May 9, 2012 (Applicatns—Arizona Technology Enterprises (AZTE); Inventors—Li et al,; (7 pages).
Response to Office Action (and English Translation) filed with the Chinese Patent Office on Jan. 13, 2014 for Pat. App. No. 201080024040.X filed Apr. 6, 2010 and published as Cn1 024491 08A on May 9, 2012 (Applicants—Arizona Technology Enterprises (AZTE); Inventors—Li et al,; (16 pages).
Official Action issued by the Japanese Patent Office on Mar. 13, 2014 for Pat. App. No. 2012-504779 filed Apr. 6, 2010 and published as JP 2012-522843 on Sep. 27, 2012 (Applicants—Arizona Technology Enterprises (AZTE); Inventors—Li et al; (5 pages).
Official Action (English translation only) issued by the Japanese Patent Office on Mar. 13, 2014 for Pat. App. No. 2012-504779 filed Apr. 6, 2010 and published as JP 2012-522843 on Sep. 27, 2012 (Applicants—Arizona Technology Enterprises (AZTE); Inventors—Li et al) (8 page).
Wong; Challenges in organometallic research—Great opportunity for solar cells and OLEDs, Journal of Organometallic Chemistry, 2009, 694, 2644-2647.
JP2009267244, English Translation from EPO, Nov. 2009, 80 pages.
JP2010135689, English translation from EPO, Jun. 2010, 95 pages.
Ying Yang et al., "Induction of Circularly Polarized Electroluminescence from an Achiral Light-Emitting Polymer via a Chiral Small-Molecule Dopant," Advanced Materials, vol. 25, Issue 18, May 14, 2013, pp. 2624-2628.
Barry O'Brien et al.: White organic light emitting diodes using Pt-based red, green and blue phosphorescent dopants. Proc. SPIE, vol. 8829, pp. 1-6 Aug. 25, 2013.
Baldo et al., "Highly Efficient Phosphorescent Emission from Organic Electroluminescent Devices," Nature, vol. 395, Sep. 10, 1998, pp. 151-154.
Examiner Yukai Fan, First Office Action (and English Translation) for Chinese Patent Application No. 201180024348.9 issued Feb. 7, 2014, 12 pages.
Chi et al., "Transition-metal phosphors with cyclometalating ligands: fundamentals and applications", Chemical Society Reviews, vol. 39, No. 2, Feb. 2010, pp. 638-655.
Satake et al., "Interconvertible Cationic and Neutral Pyridinylimidazole η3-Allylpalladium Complexes. Structural Assignment by 1H, 13C, and 15N NMR and X-ray Diffraction, Organometallics", vol. 18, No. 24, 1999, pp. 5108-5111.
Baldo et al., "Very high-efficiency green organic light-emitting devices based on electrophosphorescence," Applied Physics Letters, vol. 75, No. 1, Jul. 5, 1999, pp. 4-6.
Xiao-Chu Hang et al., "Highly Efficient Blue-Emitting Cyclometalated Platinum(II) Complexes," Angewandte Chemie, International Edition, vol. 52, No. 26, Jun. 24, 2013, pp. 6753-6756.
Examiner Quan Wang, Second Office Action (and English Translation) for Chinese Patent Application No. 201180024348.9, issued Dec. 26, 2014, 12 pages.
International Search Report and Written Opinion mailed by the International Searching Authority on May 14, 2015 for PCT/US2015/018195 filed Feb. 27, 2015, 17 pages.

Ayan Maity et al., "Room-temperature synthesis of cyclometalated iridium(III) complexes; kinetic isomers and reactive functionalities", Chem. Sci., vol. 4, 2013, pp. 1175-1181.
Shiro Koseki et al., "Spin-orbit coupling analyses of the geometrical effects on phosphorescence in Ir(ppy)3 and its derivatives", J. Phys. Chem. C, vol. 117, 2013, pp. 5314-5327.
Ji Hyun Seo et al., "Efficient blue-green organic light-emitting diodes based on heteroleptic tris-cyclometalated iridium (III) complexes", Thin Solid Films, vol. 517, 2009, pp. 1807-1810.
Official Action (and English Translation) issued by the Japanese Patent Office on Mar. 11, 2015 for Pat. App. No. 2013-508083 filed May 2, 2011, 15 pages.
Vanessa Wood et al., "Colloidal quantum dot light-emitting devices," Nano Reviews, vol. 1, 2010, 8 pages.
Glauco Ponterini et al., "Comparison of Radiationless Decay Processes in Osmium and Platinum Porphyrins," J. Am. Chem. Soc., vol. 105, No. 14, 1983, pp. 4639-4645.
Shizuo Tokito et al., "Confinement of triplet energy on phosphorescent molecules for highly-efficient organic blue-light-emitting devices," Applied Physics Letters, vol. 83, No. 3, Jul. 21, 2003, pp. 569-571.
Brian W. D'Andrade et al., "Controlling Exciton Diffusion in Multilayer White Phosphorescent Organic Light Emitting Devices," Adv. Mater., vol. 14, No. 2, Jan. 16, 2002, pp. 147-151.
Dileep A. K. Vezzu et al., "Highly Luminescent Tetradentate Bis-Cyclometalated Platinum Complexes: Design, Synthesis, Structure, Photophysics, and Electroluminescence Application," Inorg. Chem., vol. 49, 2010, pp. 5107-5119.
Evan L. Williams et al., "Excimer-Based White Phosphorescent Organic Light Emitting Diodes with Nearly 100% Internal Quantum Efficiency," Adv. Mater., vol. 19, 2007, pp. 197-202.
Shih-Chun Lo et al., "High-Triplet-Energy Dendrons: Enhancing the Luminescence of Deep Blue Phosphorescent Indium(III) Complexes," J. Am. Chem. Soc., vol. 131, 2009, pp. 16681-16688.
Jan Kalinowski et al., "Light-emitting devices based on organometallic platinum complexes as emitters," Coordination Chemistry Reviews, vol. 255, 2011, pp. 2401-2425.
Ke Feng et al. "Norbornene-Based Copolymers Containing Platinum Complexes and Bis(carbazolyl)benzene Groups in Their Side-Chains," Macromolecules, vol. 42, 2009, pp. 6855-6864.
Chi-Ming Che et al., "Photophysical Properties and OLED Applications of Phosphorescent Platinum(II) Schiff Base Complexes," Chem. Eur. J., vol. 16, 2010, pp. 233-247.
Stephen R. Forrest, "The path to ubiquitous and low-cost organic electronic appliances on plastic," Nature, vol. 428, Apr. 29, 2004, pp. 911-918.
Nicholas R. Evans et al., "Triplet Energy Back Transfer in Conjugated Polymers with Pendant Phosphorescent Iridium Complexes," J. Am. Chem. Soc., vol. 128, 2006, pp. 6647-6656.
Xiaofan Ren et al., "Ultrahigh Energy Gap Hosts in Deep Blue Organic Electrophosphorescent Devices," Chem. Mater, vol. 16, 2004, pp. 4743-4747.
Jeonghun Kwak et al., "Bright and Efficient Full-Color Colloidal Quantum Dot Light-Emitting Diodes Using an Inverted Device Structure," Nano Lett., 2012, Vo. 12, pp. 2362-2366.
Hirohiko Fukagawa et al., "Highly Efficient and Stable Red Phosphorescent Organic Light-Emitting Diodes Using Platinum Complexes," Adv. Mater., 2012, vol. 24, pp. 5099-5103.
Eric Turner et al., "Cyclometalated Platinum Complexes with Luminescent Quantum Yields Approaching 100%," Inorg. Chem., 2013, vol. 52, pp. 7344-7351.
Steven C. F. Kui et al., "Robust Phosphorescent Platinum(II) Complexes Containing Tetradentate OÔNÔCÔN Ligands: Excimeric Excited State and Application in Organic White-Light-Emitting Diodes," Chem. Eur. J., 2013, vol. 19, pp. 69-73.
Steven C. F. Kui et al., "Robust phosphorescent platinum(II) complexes with tetradentate OÔNÔCÔN ligands: high efficiency OLEDs with excellent efficiency stability," Chem. Commun., 2013, vol. 49, pp. 1497-1499.
Kai Li et al., "Light-emitting platinum(II) complexes supported by tetradentate dianionic bis(N-heterocyclic carbene) ligands: towards robust blue electrophosphors," Chem. Sci., 2013, vol. 4, pp. 2630-2644.

(56) References Cited

OTHER PUBLICATIONS

Dorwald, "Side Reactions in Organic Synthesis: A Guide to Successful Synthesis Design," Chapter 1, 2005 Wiley-VCH Verlag GmbH & Co. KGaA, Wienheim, 32 pages.

Examiner Quan Wang, Third Office Action (and English Translation) for Chinese Patent Application No. 201180024348.9, issued Sep. 2, 2015, 7 pages.

Murakami, JP 2007258550, English machine translation from EPO, Oct. 4, 2007, 80 pages.

Murakami, JP 2007324309, English machine translation from EPO, Dec. 13, 2007, 89 pages.

Final Rejection (and English Translation) issued by the Japanese Patent Office on Oct. 30, 2015 for Pat. App. No. 2013-508083, 6 pages.

\* cited by examiner

SYNTHESIS OF FOUR COORDINATED GOLD COMPLEXES AND THEIR APPLICATIONS IN LIGHT EMITTING DEVICES THEREOF

CROSS-REFERENCE TO RELATED APPLICATIONS

The present application is a U.S. National Phase Application of International Application No. PCT/US2011/034782, filed May 2, 2011, which claims priority to U.S. Patent Application No. 61/329,687, filed Apr. 30, 2010, all of which applications are incorporated herein fully by this reference.

BACKGROUND

1. Technical Field

The present disclosure relates to gold complexes which are capable of absorbing and/or emitting light and are thus useful as an emissive or absorption material in a device.

2. Technical Background

Compounds capable of absorbing and/or emitting light are ideally suited for use in a wide variety of optical and electro-optical devices, including photo-absorbing devices such as solar- and photo-sensitive devices, photo-emitting devices, such as organic light emitting diodes (OLEDs), or devices capable of both photo-absorption and emission. Much research has been devoted to the discovery and optimization of organic and organometallic materials for use in optical and electro-optical devices. Generally, research in this area aims to accomplish a number of goals, including improvements in absorption and emission efficiency, as well as improvements in processing ability, among others.

Despite significant advances in research devoted to optical and electro-optical materials, many current devices comprising organic or organometallic materials have yet to be optimized. Many materials currently used in optical and electro-optical devices have a number disadvantages, including poor processing ability, inefficient emission or absorption, and less than ideal stability, among others. Thus, a need exists for new materials which exhibit improved performance in optical and electro-optical devices. This need and other needs are satisfied by the present invention.

SUMMARY

The present invention relates to gold complexes that exhibit photo-absorption and photo-emission, to methods of making such compounds, and to applications thereof, including optical devices comprising the compounds.

In one embodiment, the compounds are represented by the formula:

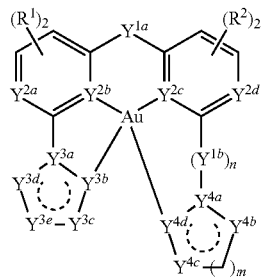

wherein each $R^1$ and $R^2$ in $(R^1)_2$ and $(R^2)_2$ independently represents hydrogen, optionally substituted $C_1$-$C_4$ alkyl, halogen, hydroxyl, amino, nitro, or thiol;

$Y^{1a}$ represents O, S, $NR^{4a}$, wherein $R^{4a}$ represents optionally substituted $C_1$-$C_4$ alkyl; $Si(R^{4b})_2$, wherein each $R^{4b}$ in $(R^{4b})_2$ independently represents optionally substituted $C_1$-$C_4$ alkyl; or $C(R^{4c})_2$, wherein each $R^{4c}$ in $(R^{4c})_2$ represents hydrogen or optionally substituted $C_1$-$C_4$ alkyl;

n is an integer 0 or 1;

$Y^{1b}$, when present, represents O, S, $NR^{5a}$, wherein $R^{5a}$ represents optionally substituted $C_1$-$C_4$ alkyl; $Si(R^{5b})_2$, wherein each $R^{5b}$ in $(R^{5b})_2$ independently represents optionally substituted $C_1$-$C_4$ alkyl; or $C(R^{5c})_2$, wherein each $R^{5c}$ in $(R^{5c})_2$ represents hydrogen or optionally substituted $C_1$-$C_4$ alkyl;

each of $Y^{2a}$, $Y^{2b}$, $Y^{2c}$, and $Y^{2d}$ independently represents N, $NR^{6a}$, or $CR^{6b}$, wherein each of $R^{6a}$ and $R^{6b}$ independently represents hydrogen, optionally substituted $C_1$-$C_4$ alkyl, halogen, hydroxyl, amino, nitro, or thiol;

each of $Y^{3a}$, $Y^{3b}$, $Y^{3c}$, $Y^{3d}$, $Y^{3e}$, $Y^{4a}$, $Y^{4b}$, $Y^{4c}$, and $Y^{4d}$ independently represents N, O, S, $NR^{6a}$, $CR^{6b}$, wherein each of $R^{6a}$ and $R^{6b}$ independently represents hydrogen or optionally substituted $C_1$-$C_4$ alkyl; or $Z(R^{6c})_2$, wherein Z is C or Si, and wherein each $R^{6c}$ in $(R^{6c})_2$ independently represents hydrogen or optionally substituted $C_1$-$C_4$ alkyl;

wherein m is an integer 1 or 2;

wherein the open dotted circle

indicates partial or full unsaturation of the ring with which it is associated;

provided that if m is 1, each of $Y^{2a}$ and $Y^{2d}$ is CH and either of $Y^{2b}$ or $Y^{2c}$ is N, then at least one of $Y^{4a}$, $Y^{4b}$, $Y^{3a}$, or $Y^{3d}$ is not N; and provided that if n is 0, m is 2, each of $Y^{2a}$ and $Y^{2d}$ is CH, and either of $Y^{2b}$ or $Y^{2c}$ is N, then at least one of $Y^{3b}$ or $Y^{3c}$ is not N.

Also disclosed are optical devices, such as organic light emitting devices, photovoltaic devices (e.g., solar cells), and luminescent display devices that comprise one or more compounds of the invention as a functional material, such as a light-emitter or absorber, or both.

BRIEF DESCRIPTION OF THE FIGURES

The accompanying figures, which are incorporated in and constitute a part of this specification, illustrate several aspects and together with the description serve to explain the principles of the invention.

Figure 1:
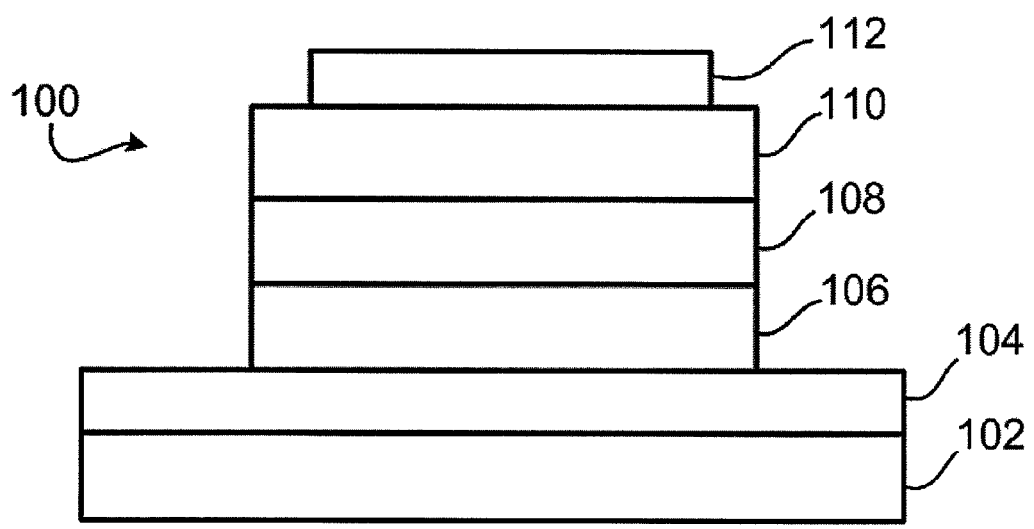
FIG. 1 is a drawing of a cross-section of an exemplary organic light-emitting diode (OLED).
Figure 2A:
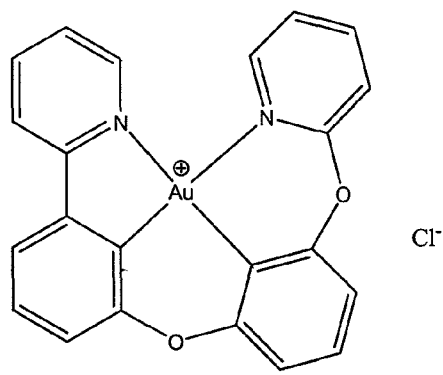
FIG. 2 illustrates: (A) an exemplary four coordinated gold complex, 2-(3-(pyridin-2-yl)phenoxy)-6-(pyridin-2-yloxy) phenyl]Au(III)Cl, and (B) the room temperature emission spectrum thereof in untreated (not degassed) dichloromethane (DCM) and degassed (bubbled) DCM.
Figure 2B:
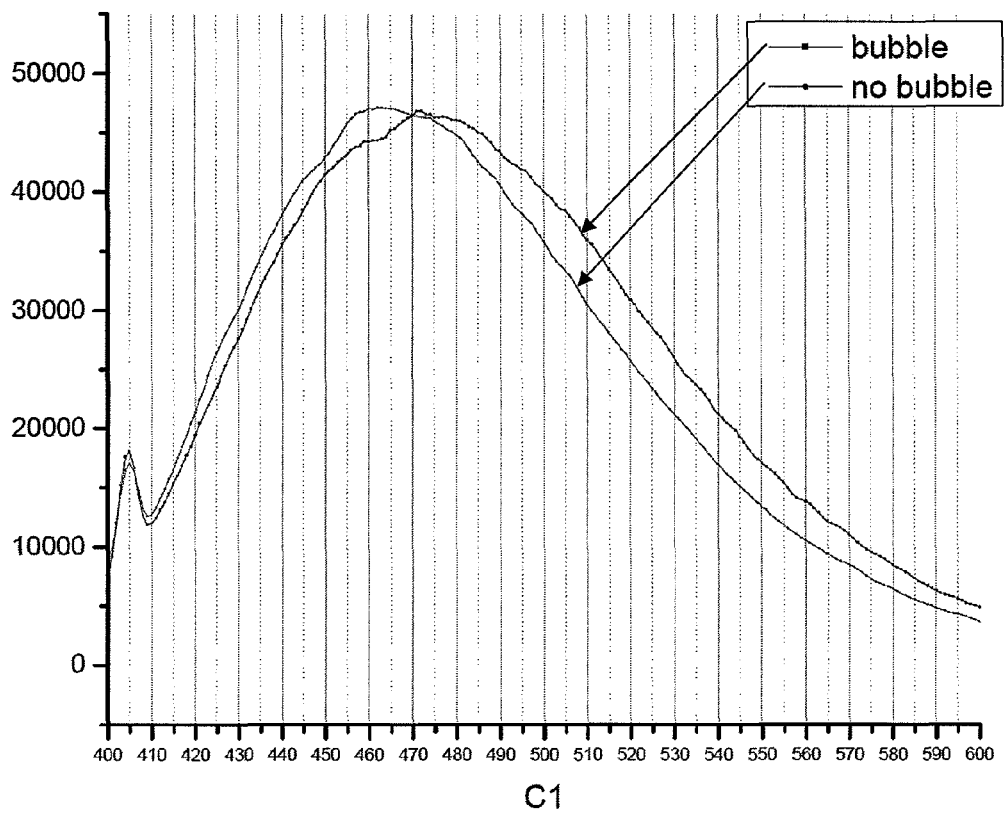

Additional aspects of the invention will be set forth in part in the description which follows, and in part will be obvious from the description, or can be learned by practice of the invention. The advantages of the invention will be realized and attained by means of the elements and combinations particularly pointed out in the appended claims. It is to be understood that both the foregoing general description and the following detailed description are exemplary and explanatory only and are not restrictive of the invention, as claimed.

DESCRIPTION

The present invention can be understood more readily by reference to the following detailed description of the invention and the Examples included therein.

Before the present compounds, devices, and/or methods are disclosed and described, it is to be understood that they are not limited to specific synthetic methods unless otherwise specified, or to particular reagents unless otherwise specified, as such can, of course, vary. It is also to be understood that the terminology used herein is for the purpose of describing particular aspects only and is not intended to be limiting. Although any methods and materials similar or equivalent to those described herein can be used in the practice or testing of the present invention, example methods and materials are now described.

As used in the specification and the appended claims, the singular forms "a," "an" and "the" include plural referents unless the context clearly dictates otherwise. Thus, for example, reference to "a component" includes mixtures of two or more components.

Ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

As used herein, the terms "optional" or "optionally" means that the subsequently described event or circumstance can or can not occur, and that the description includes instances where said event or circumstance occurs and instances where it does not.

The term "alkyl" as used herein is a branched or unbranched saturated hydrocarbon group of 1 to 24 carbon atoms, such as methyl, ethyl, n-propyl, isopropyl, n-butyl, isobutyl, s-butyl, t-butyl, n-pentyl, isopentyl, s-pentyl, neopentyl, hexyl, heptyl, octyl, nonyl, decyl, dodecyl, tetradecyl, hexadecyl, eicosyl, tetracosyl, and the like. The alkyl group can be cyclic or acyclic. The alkyl group can be branched or unbranched. The alkyl group can also be substituted or unsubstituted. For example, the alkyl group can be substituted with one or more groups including, but not limited to, optionally substituted alkyl, cycloalkyl, alkoxy, amino, ether, halide, hydroxy, nitro, silyl, sulfo-oxo, or thiol, as described herein. A "lower alkyl" group is an alkyl group containing from one to six (e.g., from one to four) carbon atoms.

The terms "amine" or "amino" as used herein are represented by the formula $NA^1A^2A^3$, where $A^1$, $A^2$, and $A^3$ can be, independently, hydrogen or optionally substituted alkyl, cycloalkyl, alkenyl, cycloalkenyl, alkynyl, cycloalkynyl, aryl, or heteroaryl group as described herein.

The term "halide" as used herein refers to the halogens fluorine, chlorine, bromine, and iodine.

The term "hydroxyl" as used herein is represented by the formula —OH.

The term "nitro" as used herein is represented by the formula —$NO_2$.

The term "nitrile" as used herein is represented by the formula —CN.

The term "thiol" as used herein is represented by the formula —SH.

Disclosed are the components to be used to prepare the compositions of the invention as well as the compositions themselves to be used within the methods disclosed herein. These and other materials are disclosed herein, and it is understood that when combinations, subsets, interactions, groups, etc. of these materials are disclosed that while specific reference of each various individual and collective combinations and permutation of these compounds can not be explicitly disclosed, each is specifically contemplated and described herein. For example, if a particular compound is disclosed and discussed and a number of modifications that can be made to a number of molecules including the compounds are discussed, specifically contemplated is each and every combination and permutation of the compound and the modifications that are possible unless specifically indicated to the contrary. Thus, if a class of molecules A, B, and C are disclosed as well as a class of molecules D, E, and F and an example of a combination molecule, A-D is disclosed, then even if each is not individually recited each is individually and collectively contemplated meaning combinations, A-E, A-F, B-D, B-E, B-F, C-D, C-E, and C-F are considered disclosed. Likewise, any subset or combination of these is also disclosed. Thus, for example, the sub-group of A-E, B-F, and C-E would be considered disclosed. This concept applies to all aspects of this application including, but not limited to, steps in methods of making and using the compositions of the invention. Thus, if there are a variety of additional steps that can be performed it is understood that each of these additional steps can be performed with any specific embodiment or combination of embodiments of the methods of the invention.

Throughout the specification, it should be understood that where letters and/or symbols are utilized to represent atoms or functional groups, and wherein multiple instances of the same letter and/or symbol are present, that each individual instance can represent the same or different species (e.g., atom and/or functional group) than any other instance using the same letter and/or symbol. Similarly, when a metal is depicted as a portion of a chemical structure, the notation can refer to a single metal atom and/or to a plurality of atoms. In one aspect, a notation for a metal refers to a single metal atom. In another aspect, a notation for a metal refers to a plurality of metal atoms.

In one aspect, the present application discloses multidentate, such as, for example, tridentate and/or tetradentate gold (III) complexes that can be phosphorescent. In another aspect, the emission of such inventive complexes can be tuned, for example, from the ultraviolet to near-infrared, by, for example, modifying the ligand structure. In another aspect, the inventive gold complexes can have improved stability and efficiency over traditional emission complexes. In yet another aspect, the inventive gold complexes can be useful as luminescent labels in, for example, bio-applications, anti-cancer agents, photovoltaic absorbers, emitters in organic light emitting diodes (OLED), or a combination thereof.

In one aspect, the inventive gold complex of the present disclosure can be represented by the formula:
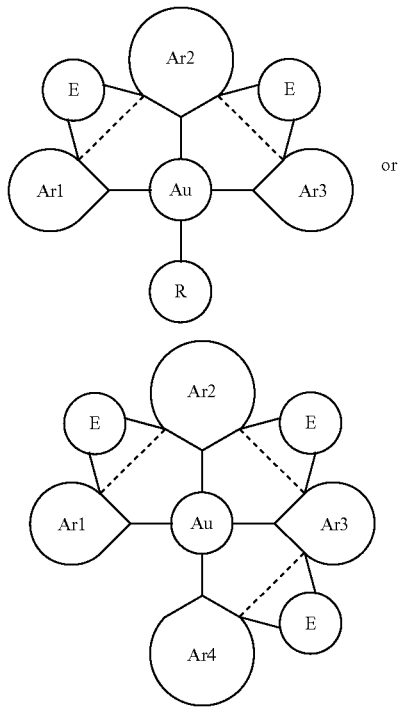
wherein Ar1, Ar2, Ar3, and Ar4, if present, represent aromatic groups, each E represents an optional linking group, such as, for example, carbon or oxygen, and R represents an ancillary ligand.
In various aspects, an ancillary ligand can comprise one or more of the following:
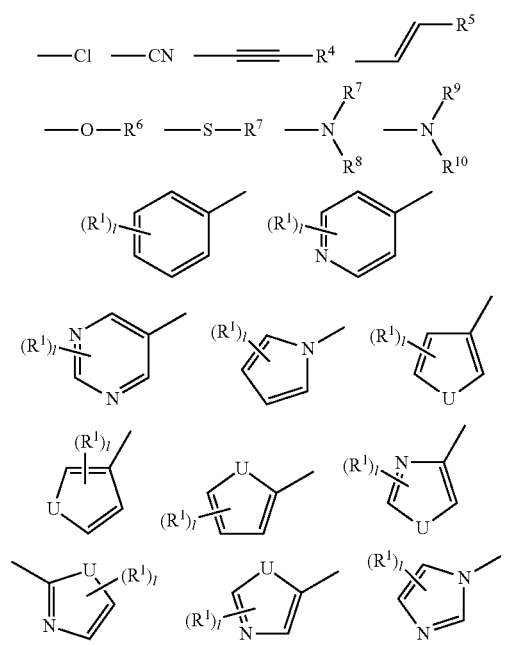
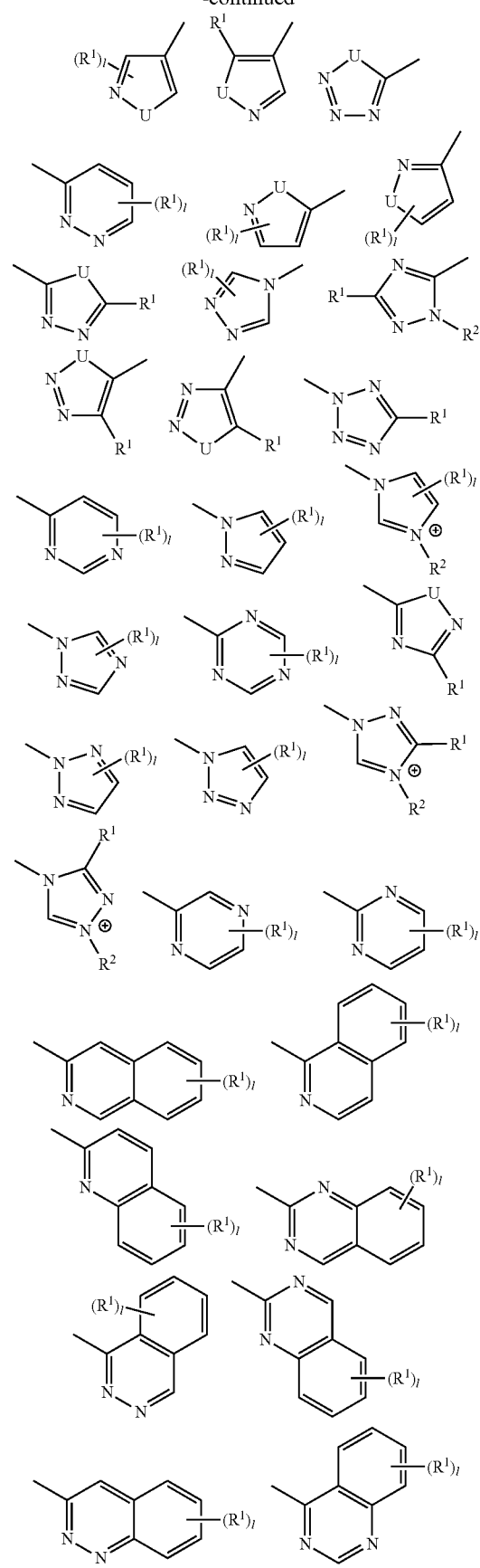

-continued

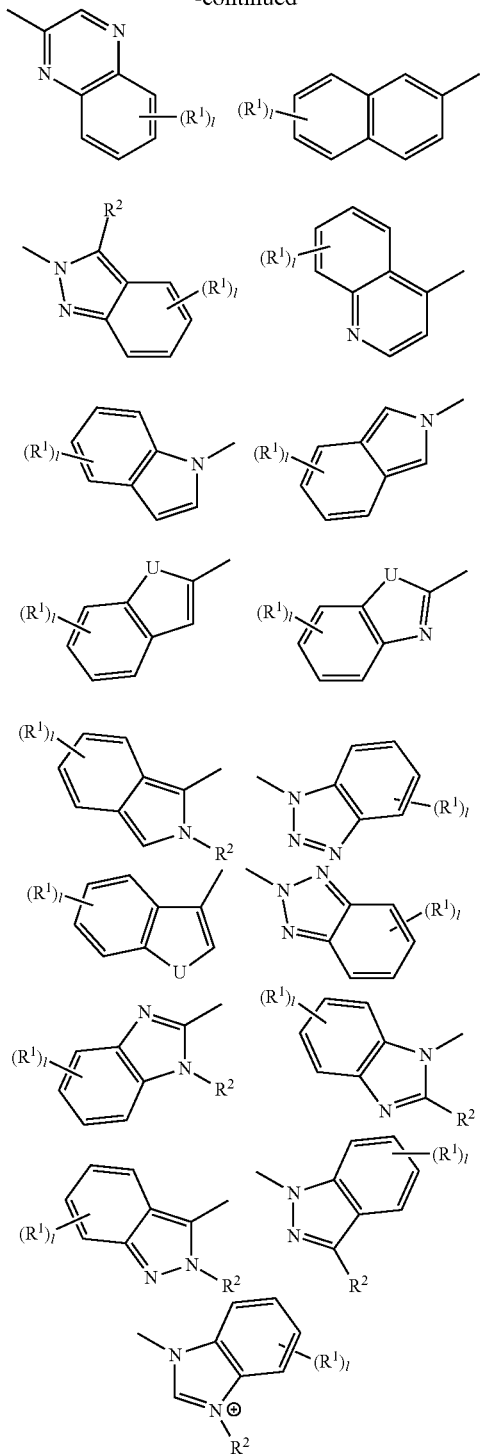

U = O, S, N—R³ wherein, $R^1$-$R^{10}$ of the ancillary ligand each independently represent a hydrogen atom, an alkyl group, a haloalkyl group, an aralkyl group, an alkenyl group, an alkynyl group, an aryl group, an amino group, a mono- or di-alkylamino group, a mono- or diaryl amino group, an alkoxy group, an aryloxy group, a heteroaryloxy group, an alkoxycarbonyl group, an acyloxy group, an acylamino group, an alkoxycarbonylamino group, an aryloxycarbonylamino group, a sulfonylamino group, a sulfamoyl group, a carbamoyl group, an alkylthio group, a sulfinyl group, a ureido group, a phosphoramide group, a hydroxyl group, a mercapto group, a halogen atom, a cyano group, a sulfo group, a carboxyl group, a nitro group, a hydrazino group, a substituted silyl group, or a polymerizable group; further, wherein a plurality of Rs exist, the number of R should be from 0 to about 4, and each R can be the same or different from any other R. In one aspect, an ancillary ligand can comprise a hydrogen atom. In another aspect, an ancillary ligand can comprise an alkyl group. In another aspect, an ancillary ligand can comprise a haloalkyl group. In another aspect, an ancillary ligand can comprise a aralkyl group. In another aspect, an ancillary ligand can comprise a alkenyl group. In another aspect, an ancillary ligand can comprise an alkynyl group. In another aspect, an ancillary ligand can comprise an aryl group. In another aspect, an ancillary ligand can comprise an amino group. In another aspect, an ancillary ligand can comprise an alkoxy group, an aryloxy group, a heteroaryloxy group, an alkoxycarbonyl group, an acyloxy group, or a combination thereof. In other aspects, an ancillary ligand can comprise an acylamino group, an alkoxycarbonylamino group, an aryloxycarbonylamino group, a sulfonylamino group, a sulfamoyl group, a carbamoyl group, an alkylthio group, a sulfinyl group, a ureido group, a phosphoramide group, a hydroxyl group, a mercapto group, a halogen atom, a cyano group, a sulfo group, a carboxyl group, a nitro group, a hydrazino group, a substituted silyl group, a polymerizable group, or a combination thereof.

In still other aspects, an ancillary ligand can comprise a group or groups difference from those specifically recited herein, and the present invention is not intended to be limited to any particular ancillary ligand.

In various aspects, specific non-limiting examples of the inventive composition can be grouped and illustrated by ligand class. In one aspect, the inventive composition can be represented by the general formula:

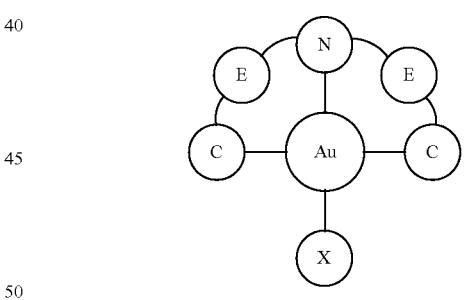

wherein Au represents gold, N represents a nitrogen substituted aromatic group, each E represents an optional linking atom, such as, for example, carbon or oxygen, X represents a halogen or other electronegative group, and each C represents an aromatic group. Specific examples of inventive compositions within this ligand class can comprise:

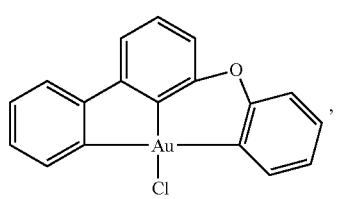

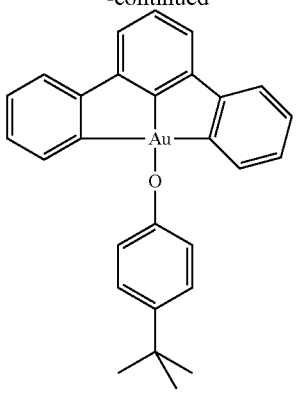

or a combination thereof.

In one aspect, the inventive composition can be represented by the general formula:

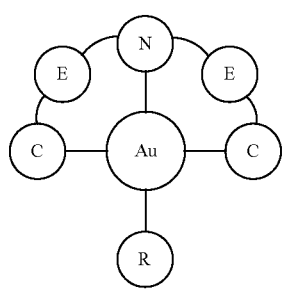

wherein Au represents gold, each E represents an optional linking atom, such as, for example, carbon or oxygen, R represents an ancillary ligand, and each C represents an aromatic group. Specific examples of inventive compositions within this ligand class can comprise:

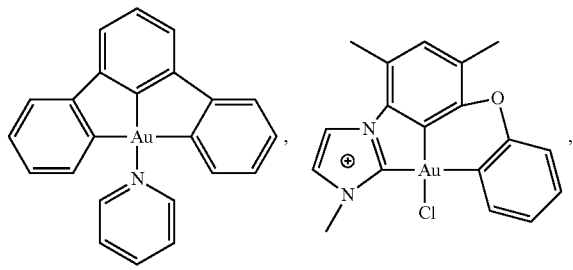

or a combination thereof.

In one aspect, the inventive composition can be represented by the general formula:

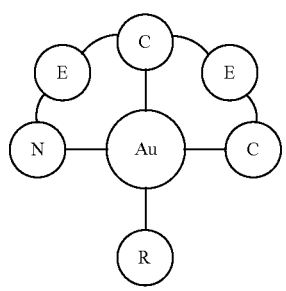

wherein Au represents gold, N represents a nitrogen substituted aromatic group, each E represents an optional linking atom, such as, for example, carbon or oxygen, R represents an ancillary ligand, and each C represents an aromatic group. Specific examples of inventive compositions within this ligand class can comprise:

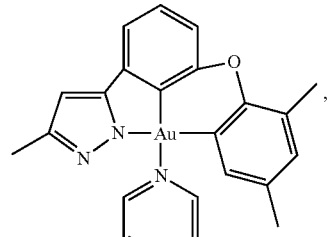

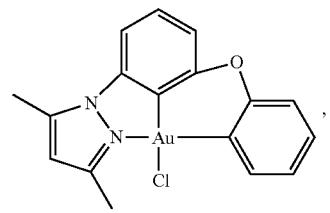

or a combination thereof.

In one aspect, the inventive composition can be represented by the general formula:

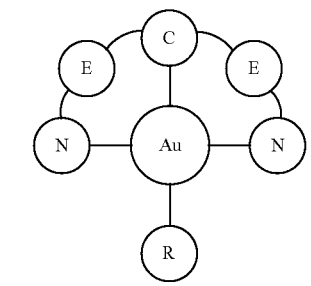

wherein Au represents gold, each N represents a nitrogen substituted aromatic group, each E represents an optional linking atom, such as, for example, carbon or oxygen, R represents an ancillary ligand, and C represents an aromatic group. Specific examples of inventive compositions within this ligand class can comprise:

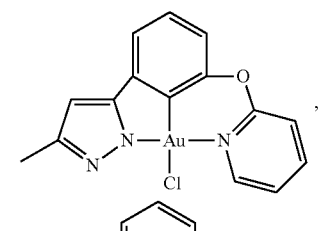

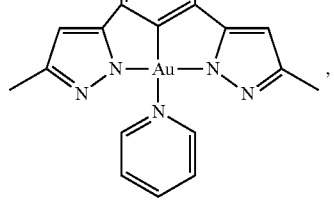

or a combination thereof.

In one aspect, the inventive composition can be represented by the general formula:

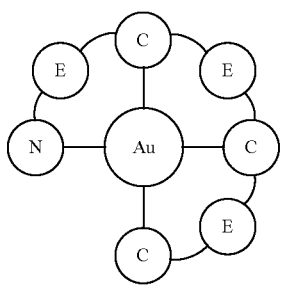

wherein Au represents gold, N represents a nitrogen substituted aromatic group, each E represents an optional linking atom, such as, for example, carbon or oxygen, and each C represents an aromatic group. Specific examples of inventive compositions within this ligand class can comprise:

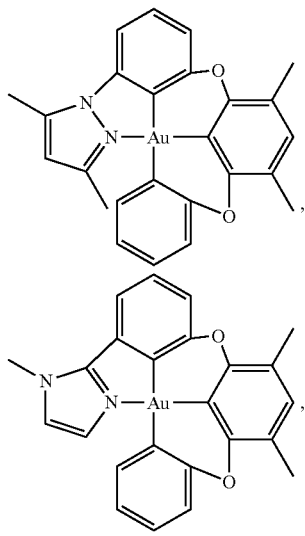

or a combination thereof.

In one aspect, the inventive composition can be represented by the general formula:

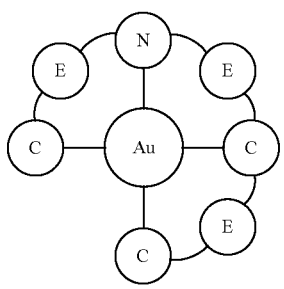

wherein Au represents gold, N represents a nitrogen substituted aromatic group, each E represents an optional linking atom, such as, for example, carbon or oxygen, and each C represents an aromatic group. Specific examples of inventive compositions within this ligand class can comprise:

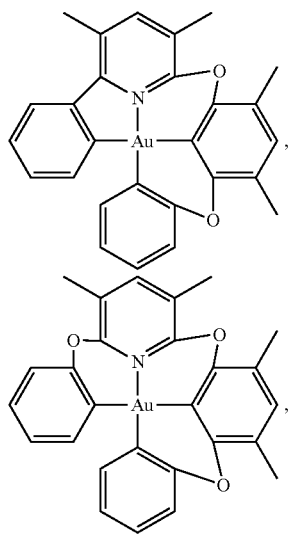

or a combination thereof.

In one aspect, the inventive composition can be represented by the general formula:

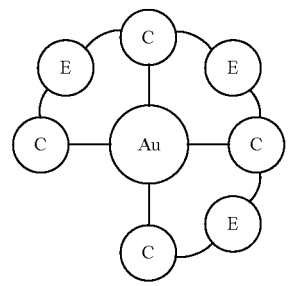

wherein Au represents gold, each E represents an optional linking atom, such as, for example, carbon or oxygen, and each C represents an aromatic group. Specific examples of inventive compositions within this ligand class can comprise:

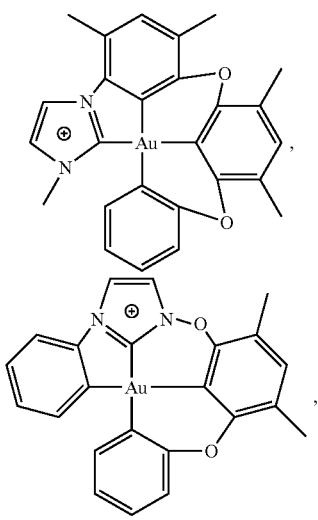

or a combination thereof.

In one aspect, the inventive composition can be represented by the general formula:

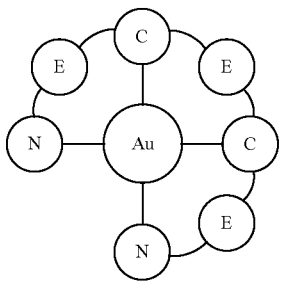

wherein Au represents gold, each N represents a nitrogen substituted aromatic group, each E represents an optional linking atom, such as, for example, carbon or oxygen, and each C represents an aromatic group. Specific examples of inventive compositions within this ligand class can comprise:

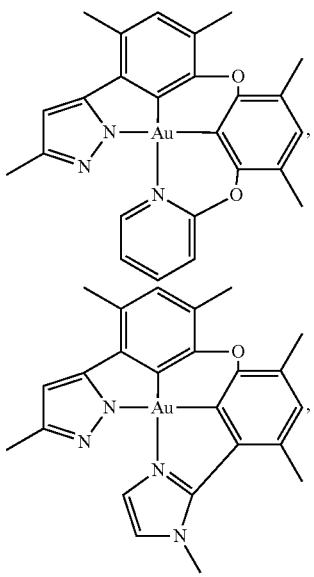

or a combination thereof.

In another aspect, the compounds of the present invention can be represented by the formula:

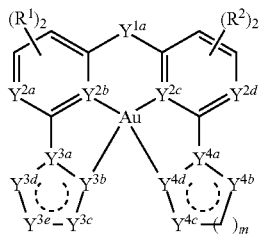

wherein each $R^1$ and $R^2$ in $(R^1)_2$ and $(R^2)_2$ independently represents hydrogen, optionally substituted $C_1$-$C_4$ alkyl, halogen, hydroxyl, amino, nitro, or thiol; $R^3$ represents methyl, ethyl, propyl, or butyl; $Y^{1a}$ represents O, S, $NR^{4a}$, wherein $R^{4a}$ represents optionally substituted $C_1$-$C_4$ alkyl; $Si(R^{4b})_2$ wherein each $R^{4b}$ in $(R^{4b})_2$ independently represents optionally substituted $C_1$-$C_4$ alkyl; or $C(R^{4c})_2$, wherein each $R^{4c}$ in $(R^{4c})_2$ represents hydrogen or optionally substituted $C_1$-$C_4$ alkyl; n is an integer 0 or 1; $Y^{1b}$, when present, represents O, S, $NR^{5a}$, wherein $R^{5a}$ represents optionally substituted $C_1$-$C_4$ alkyl; $Si(R^{5b})_2$, wherein each $R^{5b}$ in $(R^{5b})_2$ independently represents optionally substituted $C_1$-$C_4$ alkyl; or $C(R^{5c})_2$, wherein each $R^{5c}$ in $(R^{5c})_2$ represents hydrogen or optionally substituted $C_1$-$C_4$ alkyl; each of $Y^{2a}$, $Y^{2b}$, $Y^{2c}$, and $Y^{2d}$ independently represents N, $NR^{6a}$, or $CR^{6b}$, wherein each of $R^{6a}$ and $R^{6b}$ independently represents hydrogen, optionally substituted $C_1$-$C_4$ alkyl, halogen, hydroxyl, amino, nitro, or thiol; each of $Y^{3a}$, $Y^{3b}$, $Y^{3c}$, $Y^{3d}$, $Y^{3e}$, $Y^{4a}$, $Y^{4b}$, $Y^{4c}$, and $Y^{4d}$ independently represents N, O, S, $NR^{6a}$, $CR^{6b}$, wherein each of $R^{6a}$ and $R^{6b}$ independently represents hydrogen or optionally substituted $C_1$-$C_4$ alkyl; or $Z(R^{6c})_2$, wherein Z is C or Si, and wherein each $R^{6c}$ in $(R^{6c})_2$ independently represents hydrogen or optionally substituted $C_1$-$C_4$ alkyl; m is an integer 1 or 2; wherein the open dotted circle

indicates partial or full unsaturation of the ring with which it is associated.

In one embodiment of the formula above, if m is 1, either of $Y^{2a}$ or $Y^{2d}$ is CH and $Y^{2c}$ is N, then at least one of $Y^{4a}$, $Y^{4b}$, $Y^{3a}$, or $Y^{3d}$ is not N. For example, according to this embodiment, the following compound is not included in the above formula:

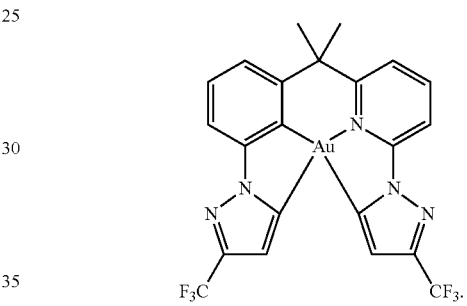

As can be seen in the preceding example above, m is 1, each of $Y^{2a}$ and $Y^{2d}$ is CH and $Y^{2c}$ is N. However, each of $Y^{4a}$, $Y^{4b}$, $Y^{3a}$, or $Y^{3d}$ is N. It follows that the preceding example, according to this embodiment, is not included within the general formula above. In the practice of this embodiment, similar analysis can be used to determine whether or not a compound is or is not included within the general formula above.

In a further embodiment of the general formula above, if n is 0, m is 2, each of $Y^{2a}$ and $Y^{2d}$ is CH, and either of $Y^{2b}$ or $Y^{2c}$ is N, then at least one of $Y^{3b}$ or $Y^{3c}$ is not N. For example, according to this embodiment, the following compound is not included in the above formula:

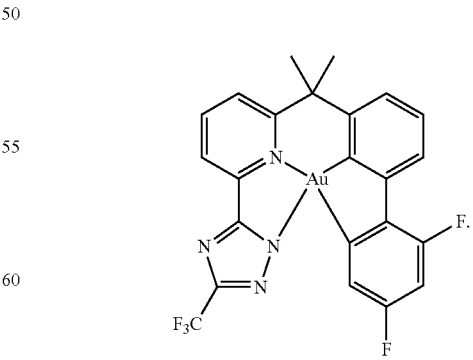

As can be seen in the preceding example above, n is 0, m is 2, each of $Y^{2a}$ and $Y^{2d}$ is CH, and $Y^{2b}$ is N. However, each of $Y^{3b}$ and $Y^{3c}$ is N. It follows that the preceding example, according to this embodiment, is not included within the general formula above. Once more, in the practice of this embodiment, similar analysis can be used to determine whether or not a compound is or is not included within the general formula above.

In one embodiment of the general formula above, the compound is represented by the formula:

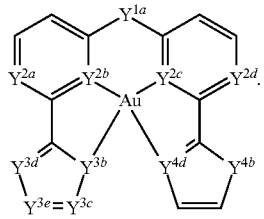

Non-limiting examples of specific embodiments within this formula include:

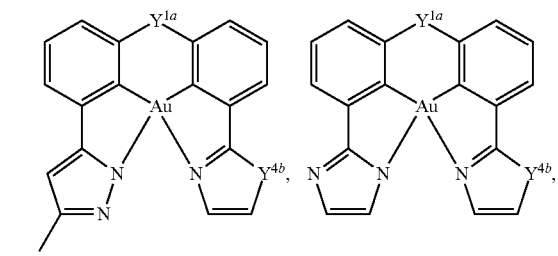

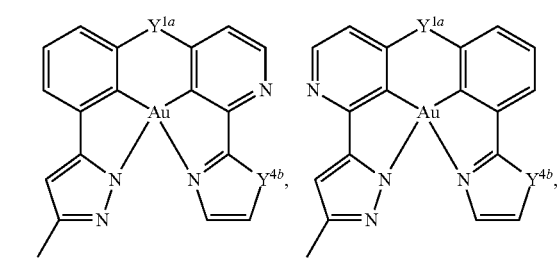

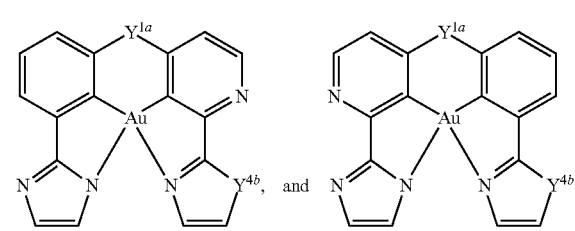

In another embodiment of the general formula above, the compound is represented by the formula:

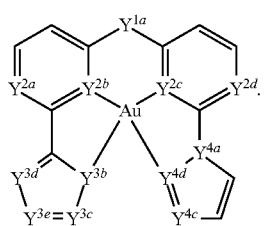

Non-limiting examples of specific embodiments within this formula include:

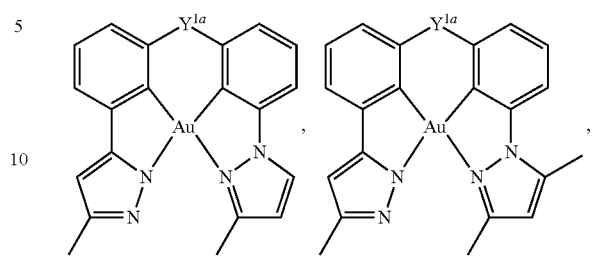

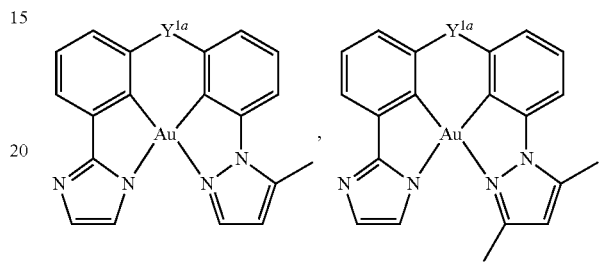

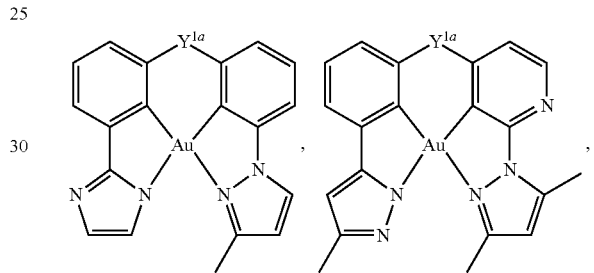

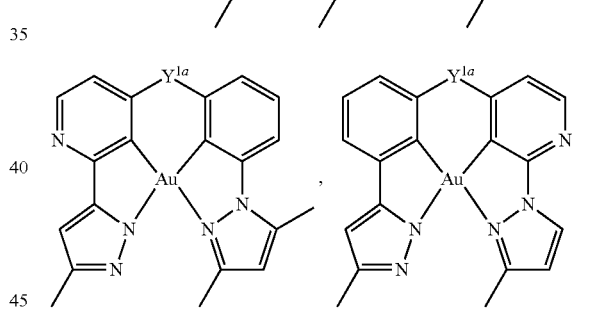

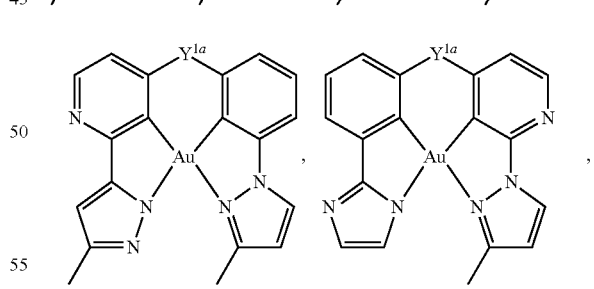

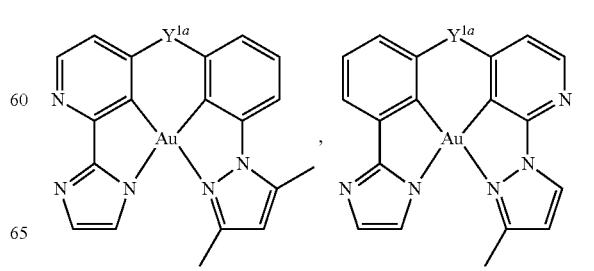

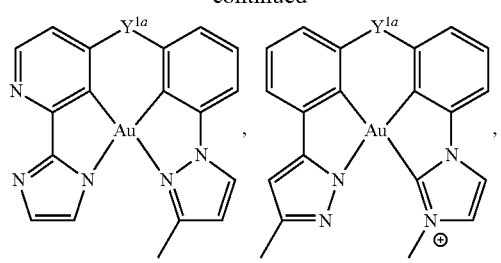
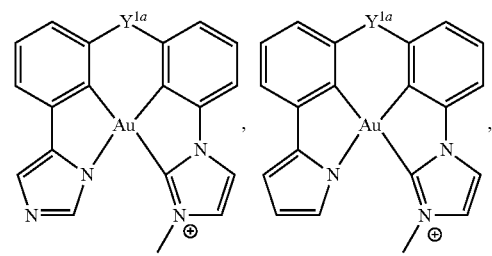
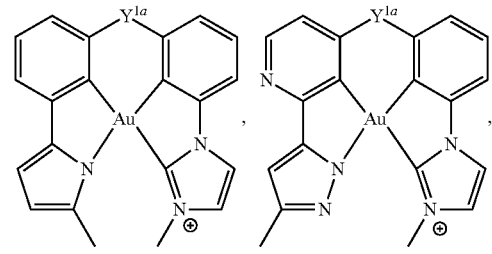
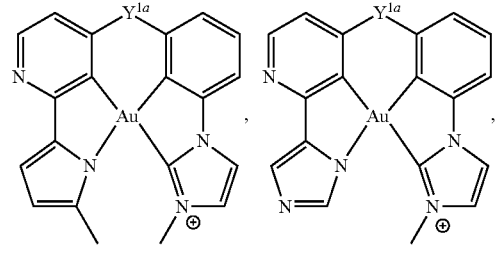
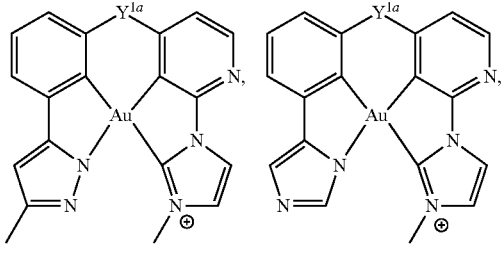
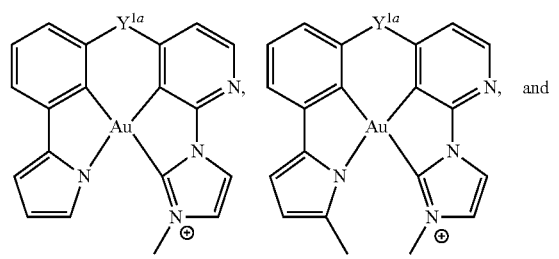
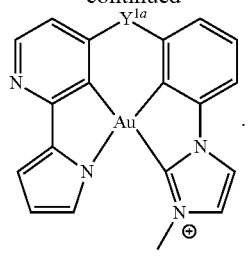
In another embodiment of the general formula above, the compound is represented by the formula:
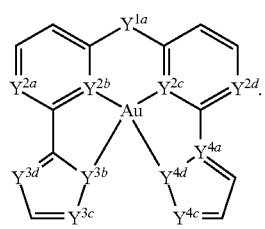
Non-limiting examples of specific embodiments within this formula include:
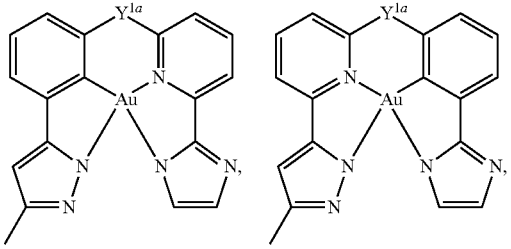
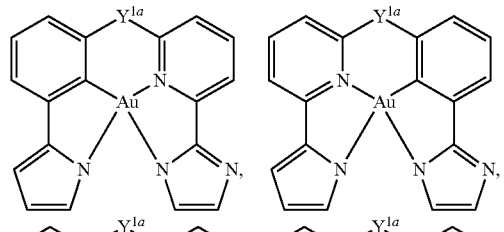
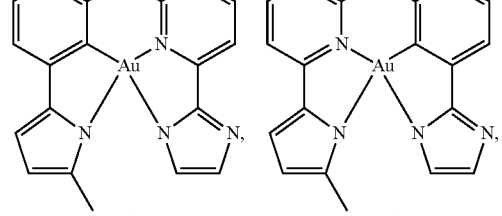
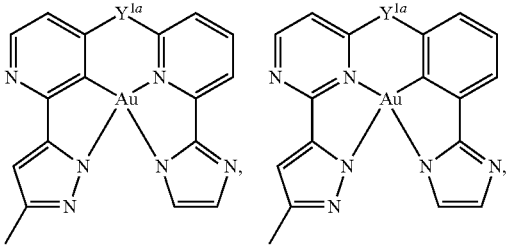

-continued
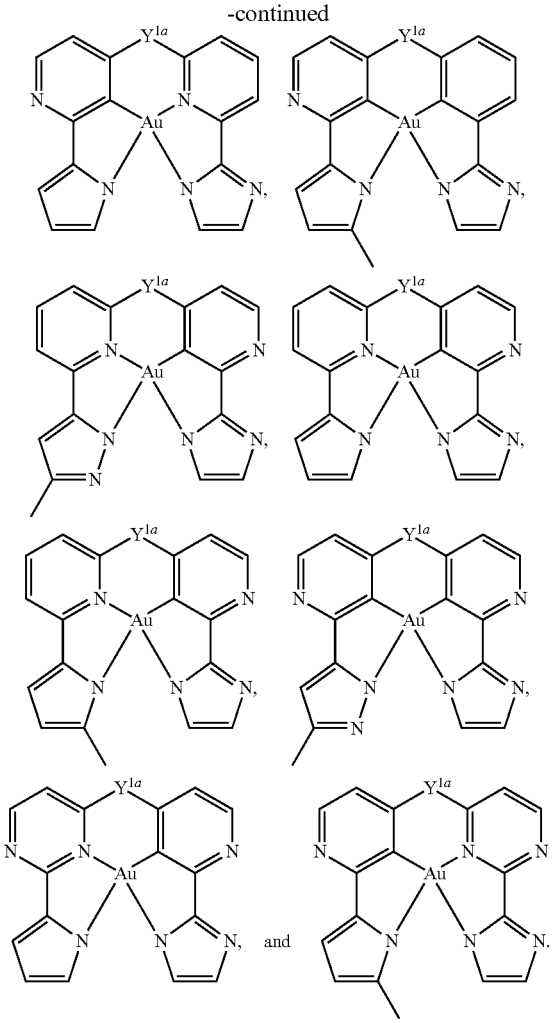
In another embodiment of the general formula above, the compound is represented by the formula:
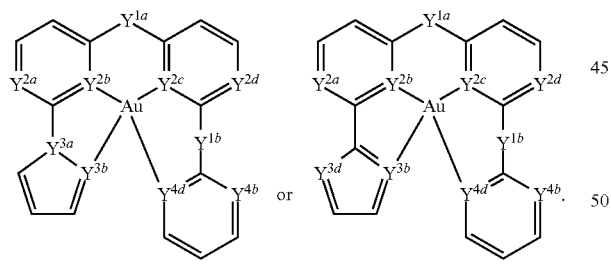
Non-limiting examples of specific embodiments within this formula include:
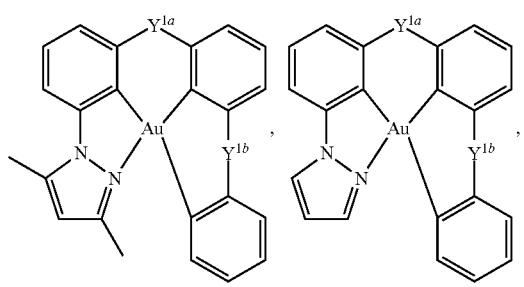
-continued
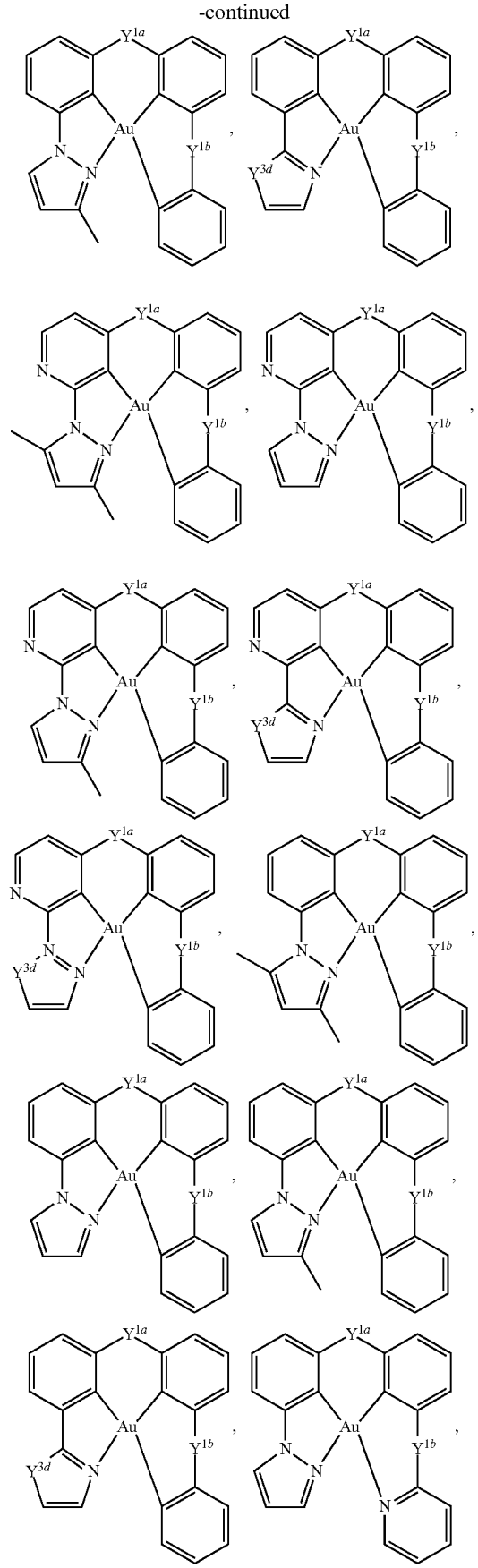

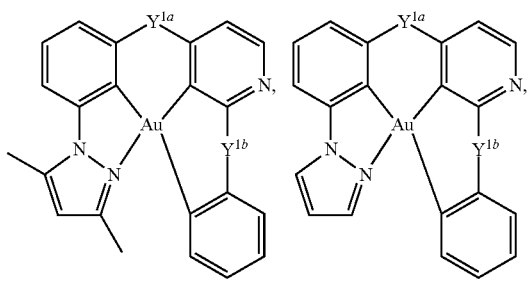
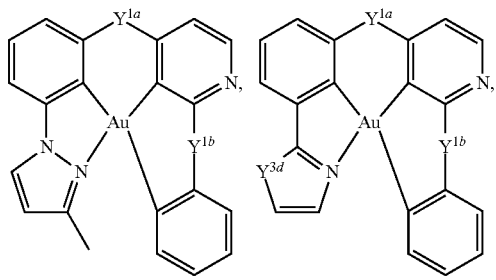
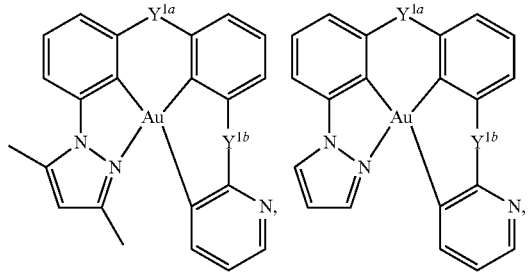
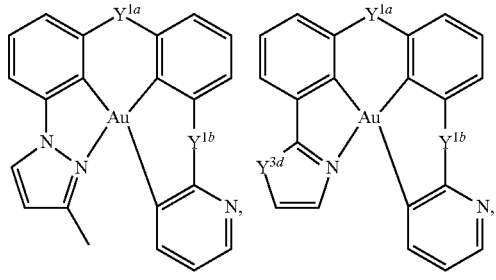
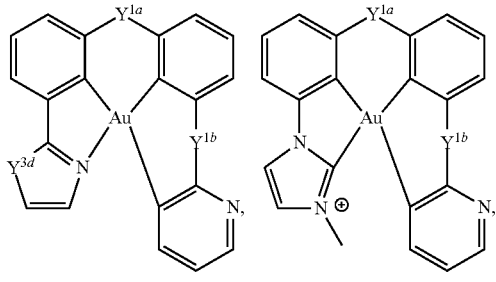
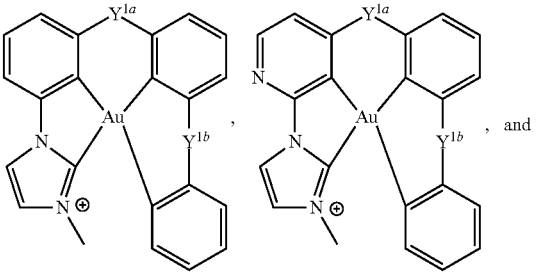
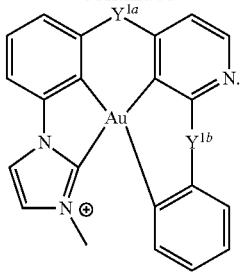
In another embodiment of the general formula above, the compound is represented by the formula:
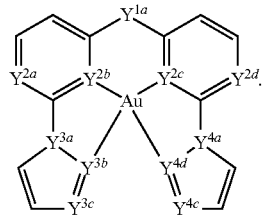
Non-limiting examples of specific embodiments within this formula include:
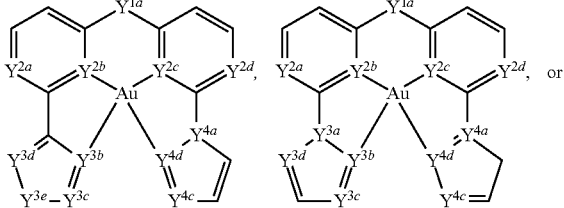
In another embodiment of the general formula above, the compound is represented by the formula:

-continued

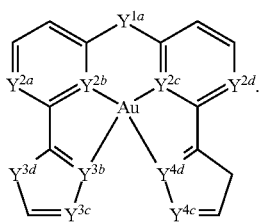

Non-limiting examples of specific embodiments within these formulae include:

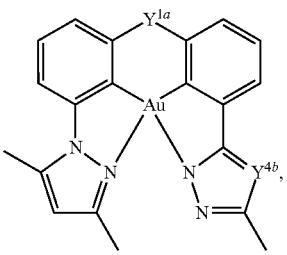

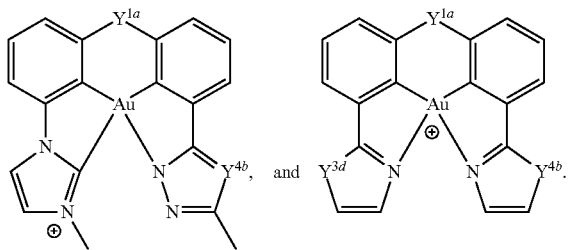

In other aspects, any one or more of the general formulas and/or specific examples recited herein can be excluded from the invention. For example, in one aspect, the formula

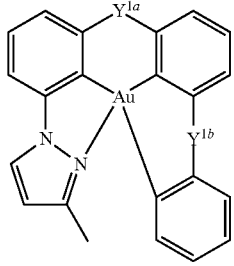

is not included in the present invention.

The compounds of the invention can be made using a variety of methods. In one embodiment, wherein $Y^{1a}$ is O, the compounds can be provided according to Scheme 1.

Scheme 1.

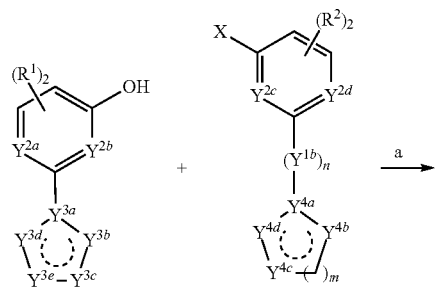

-continued

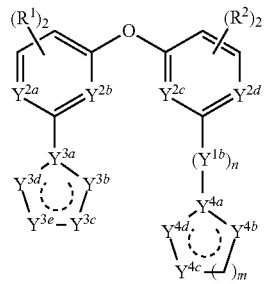

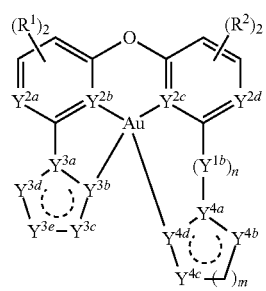

With reference to Scheme 1, step "a" can be accomplished, for example, by using a catalytic amount of a coupling reagent, such as CuI, which couples alcohols, particularly phenols, with halogenated phenyl groups. The variable "X" in Scheme 1 above represents a halogen (i.e., Cl, F, I, Br), and is preferably I when used in conjunction with Scheme 1.

In one aspect, each side of the ligand which complexes the metal can be made independently using a variety of methods, which generally depend on whether $Y^{3a}$ is N or C. With reference to Scheme 2 below, when $Y^{4a}$ is N, the precursor can be provided according to Scheme 2(A), wherein a halogenated phenyl compound is reacted with a pyrazole, imidazole, 1H-1,2,3-triazole, 1H-tetrazole, or 2H-pentazole. The halogenated phenyl compound can comprise any halogen (X), including Cl, Br, F, or I, but is preferably I, which is typically more reactive in a coupling reaction. The halogenated phenyl compound and corresponding pyrazole, imidazole, 1H-1,2,3-triazole, 1H-tetrazole, or 2H-pentazole can be coupled using a metallic or organometallic coupling agent, such as $Cu_2O$. During such a coupling reaction, it can be advantageous to include an acid scavenger, such as syn-2-pyridinealdoxime, in a small molar ratio, such as, for example, about 20 mol %.

Alternatively, when $Y^{4a}$ is C, a different protocol can be used to provide the precursor. With reference to Scheme 2(B) below, a halogenated phenyl, as discussed above is reacted with a tetrazole, 1,2,3-triazole, pyrazole, or pyrrole to achieve a carbon-carbon bond coupling, as opposed to a carbon-nitrogen bond coupling as shown in Scheme 2(A). The carbon-carbon bond coupling can also be achieved using an organometallic catalyst, such as a Pd(II) catalyst (e.g., $Pd(OAc)_2$) in a small molar ratio, which is typically used together with an excess of a salt mixture, such as KI and CuI. As one of skill in the art understands, when employing each of the coupling reactions shown in Scheme 2, it can, in one aspect, be advantageous to perform the reactions in a dry atmosphere, for example under argon, or even in a dry box to avoid moisture or oxygen inclusion.

Scheme 2.

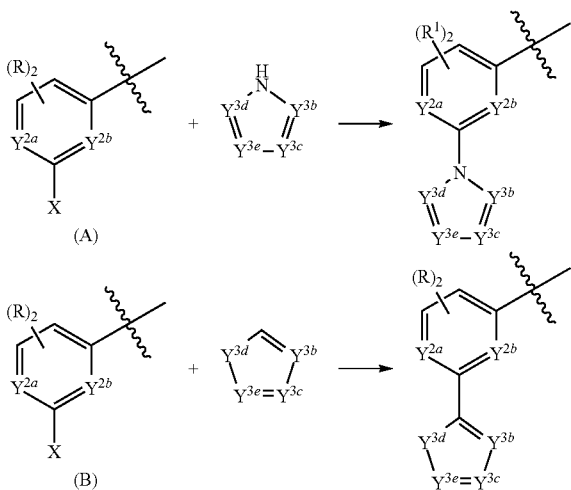

(A)

(B)

Figure 3:
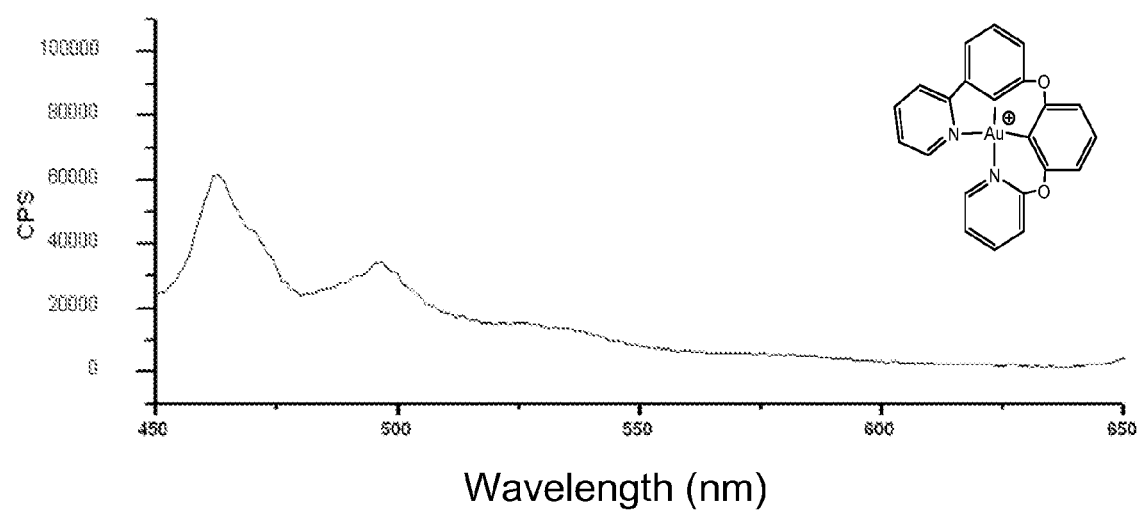
FIG. 3 is a photoluminescence spectrum produced from a specific embodiment, 2-(3-(pyridin-2-yl)phenoxy)-6-(pyridin-2-yloxy)phenyl]Au(III)Cl taken in 2-methyltetrahydrofuran at 77K.
Figure 4:
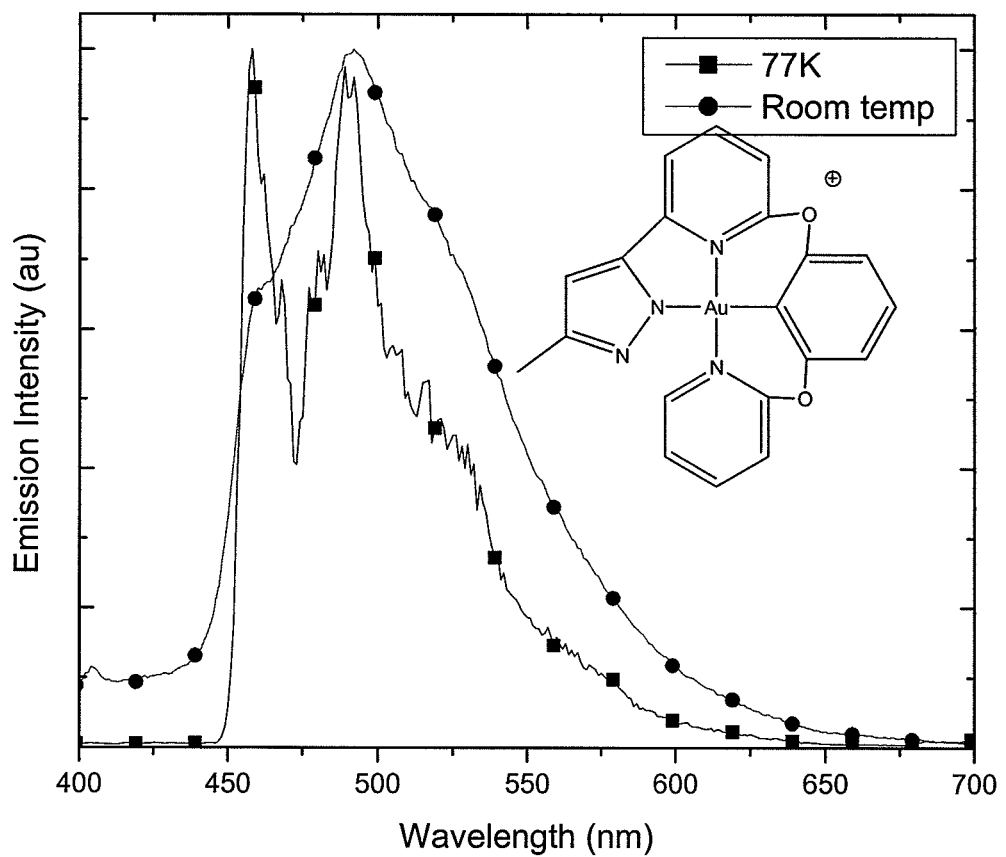
FIG. 4 is a photoluminescence spectrum produced from a specific embodiment, [2-(3-(6-(3-methyl-1H-pyrazol-5-yl) pyridin-2-yloxy)phenoxy)pyridine]Au(III)Cl taken in 2-methyltetrahydrofuran at 77K and degassed in dichloromethane at room temperature.

In one aspect, the compounds of the invention can be useful in a variety of optical applications. As light emitting materials, the compounds can be useful in organic light emitting diodes (OLED)s, luminescent devices and displays, and/or other light emitting devices. With reference to FIG. 3, for example, a specific embodiment, [2-(3-(pyridin-2-yl)phenoxy)-6-(pyridin-2-yloxy)phenyl]Au(III)Cl exhibits photoluminescence (absorption of light followed by emission of light) across a range of wavelengths from the blue to red portion of the spectrum.

In another aspect, the emission (and absorption) profile of the compounds can be tuned by varying the structure of the ligand surrounding the metal center. For example, compounds having a ligand with electron withdrawing substituents can, in one aspect, exhibit different optical properties, including emission and absorption, than compounds having a ligand with electron donating substituents. Generally, a chemical structural change affects the electronic structure of the compound, which thereby affects the absorption and emission of the compound. Thus, the compounds of the present invention can, in various aspects, be tailored or tuned to a specific application that desires a particular emission or absorption characteristic.

In one embodiment, the compounds can be used in an OLED. FIG. 1 shows a cross-sectional view of an OLED 100, which includes substrate 102 with an anode 104, which is typically a transparent material, such as indium tin oxide, a layer of hole-transporting material(s) (HTL) 106, a layer of light processing material 108, such as an emissive material (EML) including an emitter and a host, a layer of electron-transporting material(s) (ETL) 110, and a metal cathode layer 112.

In such an embodiment, the layer of light processing material 108 can comprise one or more compounds of the present invention optionally together with a host material. The host material, if present, can be any suitable host material known in the art. The emission color of an OLED is determined by the emission energy (optical energy gap) of the light processing material 108, which as discussed above can be tuned by tuning the electronic structure of the emitting compounds and/or the host material. Both the hole-transporting material in the HTL layer 106 and the electron-transporting material(s) in the ETL layer 110 can comprise any suitable hole-transporter known in the art. A selection of which is well within the purview of those skilled in the art.

It will be apparent that the compounds of the present invention can exhibit phosphorescence. Phosphorescent OLEDs (i.e., OLEDs with phosphorescent emitters) typically have higher device efficiencies that other OLEDs, such as fluorescent OLEDs. Light emitting devices based on electrophosphorescent emitters are described in more detail in WO2000/070655 to Baldo et al., which is incorporated herein by this reference for its teaching of OLEDs, and in particular phosphorescent OLEDs.

EXAMPLES

The following examples are put forth so as to provide those of ordinary skill in the art with a complete disclosure and description of how the compounds, compositions, articles, devices and/or methods claimed herein are made and evaluated, and are intended to be purely exemplary of the invention and are not intended to limit the scope of what the inventors regard as their invention. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

Example 1

Preparation of specific embodiment of [2-(3-(pyridin-2-yl)phenoxy)-6-(pyridin-2-yloxy)phenyl]Au(III)Cl Synthesis of 3-(pyridin-2-yloxy)phenol

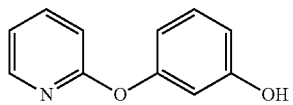 [SMILES: Oc1cccc(Oc2ccccn2)c1]

Under a nitrogen atmosphere, a pressure vessel was charged with a magnetic stir bar, resorcinol (110 mmol), 2-bromopyridine (100 mmol), 1-methylimidazole (5 mmol), and potassium carbonate (200 mmol). Pyridine (80 mL) was added and bubbled with nitrogen for 20 minutes before copper(I) iodide (10 mmol) was added and bubbled 10 minutes further. The vessel was sealed and heated to 140° C. while stirring. After 2 days, the solution was allowed to cool. The solids were filtered off and rinsed with a 50:50 mixture of toluene and methanol. The filtrate was reduced by rotary evaporation and 150 ml of water containing 10 mL glacial acetic acid was added and shaken vigorously. The water was decanted off and 50 mL of DCM was added, forming an off white precipitate which was collected by vacuum filtration and dried with ether, resulting in the pure product 3-(pyridin-2-yloxy)phenol with a 55% yield. $^1$H NMR (CDCl$_3$): 5.98 (s, 1H), 6.59 (s, 1H), 6.62-6.69 (m, 2H), 6.94 (d, 1H), f 7.02 (dd, 1H), 7.23 (vt, 1H), 7.70 (dd, 1H), 8.23 (b, 1H)

Synthesis of 2-(3-(3-bromophenoxy)phenoxy)pyridine

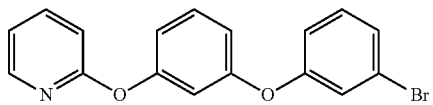 [SMILES: Brc1cccc(Oc2cccc(Oc3ccccn3)c2)c1]

Under a nitrogen atmosphere, a pressure vessel was charged with a magnetic stir bar, 3-(pyridin-2-yloxy)phenol (50 mmol), 2,6-dibromopyridine (50 mmol), 1-methylimidazole (25 mmol), and potassium carbonate (100 mmol). Toluene (80 mL) was added and bubbled with nitrogen for 20 minutes before copper(I) iodide (5 mmol) was added and the solution bubbled for 10 minutes further. The vessel was sealed and heated to 140° C. while stirring. After 2 days, the solution was allowed to cool and the solids were filtered off and rinsed with dichloromethane. The filtrate was added to a separatory funnel containing DCM and water. The water phase was washed 3 times with 75 mL DCM, and the combined organic layers were washed once with pure water. The organic layer was collected, dried with magnesium sulfate, filtered, and the filtrate reduced by rotary evaporation. The resulting oil was purified by column chromatography using DCM over silica resulting in the pure product 2-(3-(3-bromophenoxy)phenoxy)pyridine with a 60% yield. $^1$H NMR (CDCl$_3$): 6.80-6.85 (m, 2H), 6.91 (s, 1H), 6.94 (s, 1H), 6.97-7.03 (m, 2H), 7.19 (vt, 1H), 7.21-7.24 (m, 2H), 7.36 (vt, 1H), 7.70 (dd, 1H), 8.21 (dd, 1H)

Synthesis of 2-(3-(3-(pyridin-2-yl)phenoxy)phenoxy)pyridine

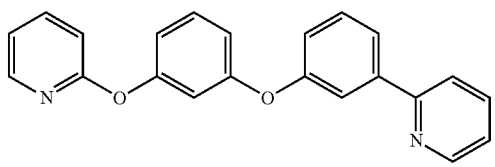 [SMILES: c1ccc(Oc2cccc(Oc3cccc(-c4ccccn4)c3)c2)nc1]

Under a nitrogen atmosphere, an oven dried three neck flask was charged with a magnetic stir bar, 2-(3-(3-bromophenoxy)phenoxy) (10 mmol), and 2-(tripropylstannyl)pyridine (10 mmol). Dry toluene (100 mL) was added and bubbled with nitrogen for 20 minutes before Tetrakis(triphenylphosphine)palladium(0) (0.5 mmol) was added, bubbled 10 minutes further, and brought to reflux for 2 days. After cooling, the contents of the flask were filtered, the liquid reduced by rotary evaporation, and the resulting oil was purified by column chromatography using DCM over silica to yield the pure product 2-(3-(3-(pyridin-2-yl)phenoxy)phenoxy)pyridine with a 65% yield. $^1$H NMR (CDCl$_3$): 6.84 (vt, 1H), 6.85-6.89 (m, 2H), 6.91 (d, 1H), 6.98 (dd, 1H), 7.11 (dd, 1H), 7.24 (dd, 1H), 7.34 (vt, 1H), 7.44 (vt, 1H), 7.66-7.78 (m, 5H), 8.19 (dd, 1H), 8.67 (dd, 1H)

Synthesis of [2-(3-(pyridin-2-yl)phenoxy)-6-(pyridin-2-yloxy)phenyl]Au(III)Cl

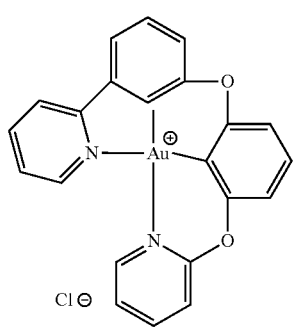

A mixture of 2-(3-(3-(pyridin-2-yl)phenoxy)phenoxy)pyridine (1 mmol), KAuCl$_4$ (1 mmol), and acetic acid (10 mL) was refluxed for 3 days. The mixture was allowed to cool to room temperature. The resulting white complex was filtered off and washed with H$_2$O, MeOH, and Et$_2$O, and dried under vacuum to [2-(3-(pyridin-2-yl)phenoxy)-6-(pyridin-2-yloxy)phenyl]Au(III)Cl.

What is claimed is:

1. A compound represented by the formula:

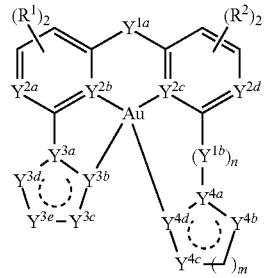

wherein each $R^1$ and $R^2$ in $(R^1)_2$ and $(R^2)_2$ independently represents hydrogen, optionally substituted $C_1$-$C_4$ alkyl, halogen, hydroxyl, amino, nitro, or thiol;

$Y^{1a}$ represents O, S, $NR^{4a}$, wherein $R^{4a}$ represents optionally substituted $C_1$-$C_4$ alkyl; $Si(R^{4b})_2$, wherein each $R^{4b}$ in $(R^{4b})_2$ independently represents optionally substituted $C_1$-$C_4$ alkyl; or $C(R^{4c})_2$, wherein each $R^{4c}$ in $(R^{4c})_2$ represents hydrogen or optionally substituted $C_1$-$C_4$ alkyl;

n is an integer 0 or 1;

$Y^{1b}$, when present, represents O, S, $NR^{5a}$, wherein $R^{5a}$ represents optionally substituted $C_1$-$C_4$ alkyl; $Si(R^{5b})_2$, wherein each $R^{5b}$ in $(R^{5b})_2$ independently represents optionally substituted $C_1$-$C_4$ alkyl; or $C(R^{5c})_2$, wherein each $R^{5c}$ in $(R^{5c})_2$ represents hydrogen or optionally substituted $C_1$-$C_4$ alkyl;

each of $Y^{2a}$, $Y^{2b}$, $Y^{2c}$, and $Y^{2d}$ independently represents N, $NR^{6a}$, or $CR^{6b}$, wherein each of $R^{6a}$ and $R^{6b}$ independently represents hydrogen, optionally substituted $C_1$-$C_4$ alkyl, halogen, hydroxyl, amino, nitro, or thiol;

each of $Y^{3a}$, $Y^{3b}$, $Y^{3c}$, $Y^{3d}$, $Y^{3e}$, $Y^{4a}$, $Y^{4b}$, $Y^{4c}$, and $Y^{4d}$ independently represents N, O, S, $NR^{6a}$, $CR^{6b}$, wherein each of $R^{6a}$ and $R^{6b}$ independently represents hydrogen or optionally substituted $C_1$-$C_4$ alkyl; or $Z(R^{6c})_2$, wherein Z is C or Si, and wherein each $R^{6c}$ in $(R^{6c})_2$ independently represents hydrogen or optionally substituted $C_1$-$C_4$ alkyl;

wherein m is an integer 1 or 2;

wherein the open dotted circle

indicates partial or full unsaturation of the ring with which it is associated;

provided that if m is 1, each of $Y^{2a}$ and $Y^{2d}$ is CH and either of $Y^{2b}$ or $Y^{2c}$ is N, then at least one of $Y^{4a}$, $Y^{4b}$, $Y^{3a}$, $Y^{3d}$ is not N; and provided that if n is 0, m is 2, each of $Y^{2a}$ and $Y^{2d}$ is CH, and either of $Y^{2b}$ or $Y^{2c}$ is N, then at least one of $Y^{3b}$ or $Y^{3c}$ is not N.

2. The compound of claim 1, which is represented by the formula:

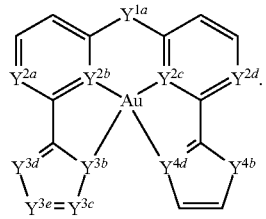

3. The compound of claim 1, which is represented by the formula:

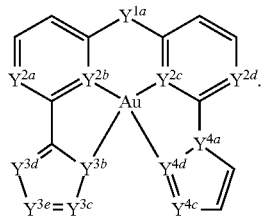

4. The compound of claim 1, which is represented by the formula:

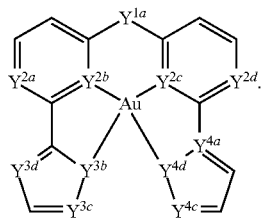

5. The compound of claim 1, which is represented by the formula:

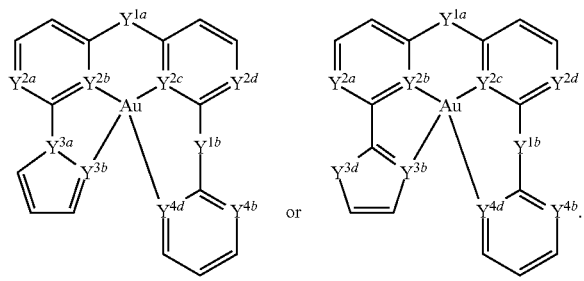

6. The compound of claim 1, which is represented by the formula:

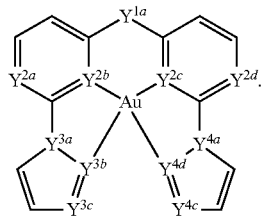

7. An organic light-emitting diode (OLED) comprising, as an emissive material, the compound of claim 1.

8. An organic photovoltaic device comprising, as a donor or acceptor material, the compound of claim 1.

9. A compound represented by the formula:

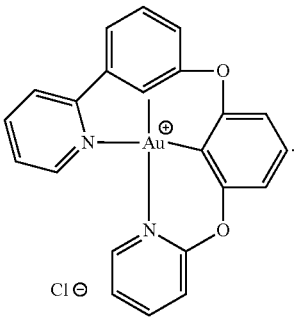

10. An organic light-emitting diode (OLED) comprising, as an emissive material, the compound of claim 9.

11. An organic photovoltaic device comprising, as a donor or acceptor material, the compound of claim 9.

\* \* \* \* \*